United States Patent [19]

Juby et al.

[11] 4,127,720

[45] Nov. 28, 1978

[54] PYRIMIDO[2,1-A]ISOQUINOLINE DERIVATIVES HAVING ANTIALLERGY ACTIVITY

[75] Inventors: Peter F. Juby, Jamesville; Thomas W. Hudyma, Manlius; Richard A. Partyka, Liverpool, all of N.Y.

[73] Assignee: Bristol-Myers Company, New York, N.Y.

[21] Appl. No.: 835,266

[22] Filed: Sep. 21, 1977

[51] Int. Cl.² .................. C07D 471/14; C07D 471/22; A61K 31/505

[52] U.S. Cl. .................................. 544/252; 544/247; 424/251

[58] Field of Search .................... 260/251 A, 256.4 F; 544/252, 247

[56] References Cited

U.S. PATENT DOCUMENTS

| 3,792,050 | 2/1974 | Hodson et al. | 260/251 A |
|---|---|---|---|
| 3,847,919 | 11/1974 | Knowles et al. | 260/256.4 F |
| 4,017,625 | 4/1977 | Kadin | 424/251 |
| 4,033,961 | 7/1977 | Schwender et al. | 260/251 A |
| 4,066,766 | 3/1978 | Kadin | 424/251 |

FOREIGN PATENT DOCUMENTS

1,451,423  10/1976  United Kingdom ................ 260/251 A

OTHER PUBLICATIONS

Cox, et al., Adv. in Drug Res., 5, 115–116 (1970).
Reimlinger, et al., Chem. Ber., 105, pp. 108–114 (1972).

*Primary Examiner*—Paul M. Coughlan, Jr.
*Assistant Examiner*—Diana G. Rivers
*Attorney, Agent, or Firm*—David M. Morse

[57] ABSTRACT

A series of novel pyrimido[2,1-a]isoquinoline derivatives is provided for use as inhibitors of allergic reactions. The compounds exhibit antiallergy activity by both oral and parenteral routes of administration.

76 Claims, No Drawings

PYRIMIDO[2,1-a]ISOQUINOLINE DERIVATIVES HAVING ANTIALLERGY ACTIVITY

BACKGROUND OF THE INVENTION

1. Field of the Invention

This invention relates to 4H-pyrimido[2,1-a]isoquinoline derivatives and to their use as inhibitors of allergic reactions.

2. Description of the Prior Art

Various medicinal agents have been employed in the treatment of allergic reactions such as bronchial asthma and allergic rhinitis which are believed to result mainly from antigen-antibody interaction. With respect to bronchial asthma, one of the most serious of these allergically-mediated diseases, bronchodilators such as theophylline, isoproterenol, epinephrine and atropine are used primarily in providing symptomatic relief. These agents, however, have undesirable side effects, e.g. cardiac stimulation and gastrointestinal distress.

With the recent introduction of disodium cromoglycate described by J. S. G. Cox, et al. in *Adv. in Drug Res.*, 5, 115–116 (1970), the physician has been provided with an agent which, when administered to asthmatic patients prior to inhalation of specific antigens, inhibits the release of mediators, e.g. histamine and SRS-A (slow-reacting-substance of anaphylaxis), believed to be responsible for the asthmatic response. While making possible a prophylactic treatment for bronchial asthma without cardiovascular side effects and thus representing a significant advance, disodium cromoglycate suffers from a major disadvantage in that it is not orally absorbed and must be administered by inhalation.

No examples of the pyrimido[2,1-a]isoquinoline derivatives of the present invention have been found in the literature. The following references illustrate structurally related compounds known in the art.

1. H. Reimlinger et al. in *Chem. Ber.*, 105, 108 (1972) describe the synthesis of several 4-oxo-4H-pyrimido[2,1-a]isoquinolines (formula A below) as well as some isomeric 2-oxo-2H-pyrimido[2,1-a]isoquinolines (formula B below).

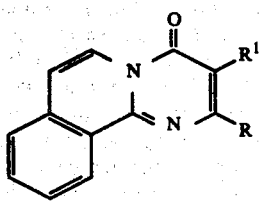

A

R = H, CH$_3$, C$_6$H$_5$
R$^1$ = H, C$_6$H$_5$

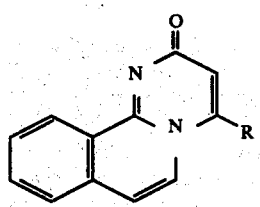

B

R = H, CH$_3$, C$_6$H$_5$

2. U.S. Pat. No. 3,792,050 discloses 2-oxo-2H pyrimido[2,1-a]isoquinolines of the formula

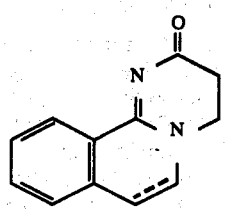

C where the dotted line represents an optional double bond. The compounds of formula C are reported to have anti-inflammatory activity.

3. U.K. Pat. No. 1,451,423 discloses 1-oxo-1H-6-substituted pyrimido[1,2-a]quinoline-2-carboxylic acids (and salts and esters thereof) of the formula

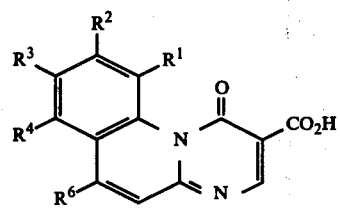

D where R$^1$, R$^2$, R$^3$ and R$^4$ are each hydrogen, fluorine, chlorine, bromine, lower alkyl, lower alkoxy, carbo(-lower)alkoxy, methylthio or methylsulphinyl or R$^2$ and R$^3$ taken together are 1,3-butadienyl, methylenedioxy or ethylenedioxy and R$^6$ is chlorine, bromine, hydroxy, lower alkoxy, alkenyloxy or alkynyloxy. The disclosed compounds D are said to possess antiallergy activity. Tetrazolyl amide derivatives of the above compounds (see formula E below) are disclosed in U.S. Pat. No. 4,017,625 as antiallergy compounds.

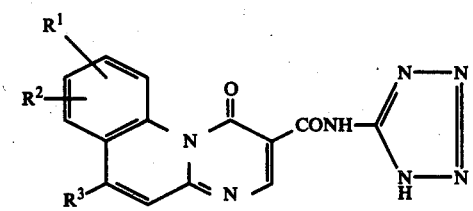

E

R$^1$/R$^2$ = hydrogen, lower alkyl, lower alkoxy, fluoro or chloro
R$^3$ = chloro, bromo or lower alkoxy
R$^1$ and R$^2$ when taken together may be alkylenedioxy.

4. U.S. Pat. No. 3,847,919 discloses a series of 1,2,3-triazolo[4',5':4,5]pyrimido[2,1-a]isoquinolin-8-ones of the formula

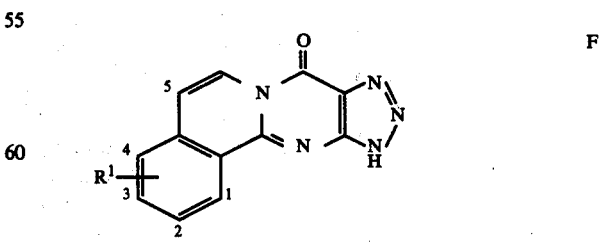

F where R$^1$ is hydrogen or an alkyl, alkoxy or benzyl substituent in the 1-, 2-, 3-, 4- or 5-position. The compounds of formula F are indicated as having antiallergy activity.

SUMMARY OF THE INVENTION

This invention relates to new therapeutically useful pyrimido[2,1-a]isoquinoline derivatives, to processes for their preparation, to pharmaceutical compositions containing them and to methods of treating allergically mediated diseases in mammals by administration of such derivatives or pharmaceutical compositions. The compounds and compositions provided by the present invention are particularly valuable in the prophylactic treatment of allergic bronchial asthma by oral administration.

The antiallergy agents provided by the present invention have the general formula

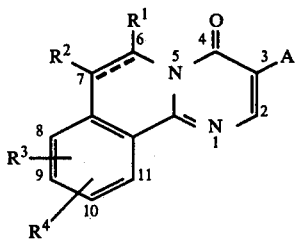

wherein A represents tetrazol-5-yl or $-CO_2R^5$ in which $R^5$ is hydrogen or the residue of an easily cleavable ester group, $R^1$ is hydrogen, (lower)alkyl or phenyl, $R^2$ is hydrogen, (lower)alkyl, (lower)alkenyl, (lower)alkynyl, hydroxy, (lower)alkoxy, $R^6-COO-$ in which $R^6$ is (lower)alkyl or phenyl, di(lower)alkoxyethyl, formylmethyl, dihydroxypropyl, hydroxyethyl, phenyl, benzyl, $C_3-C_6$ cycloalkyl, $C_1-C_2$ alkyl, $C_5-C_6$ cycloalkyl or halogen, $R^3$ and $R^4$ are each independently hydrogen, (lower)alkyl, hydroxy, (lower)alkoxy, $R^6-COO-$ in which $R^6$ is (lower)alkyl or phenyl, halogen, (lower)alkenyl or trifluoromethyl, or $R^3$ and $R^4$ taken together are methylenedioxy, and the dashed line represents an optional double bond, with the provisos that (1) $R^2$ may be halogen only where there is a double bond in the 6,7-position, (2) $R^3$ and $R^4$ taken together may not be adjacent t-butyl and (3) when either of $R^3$ or $R^4$ is trifluoromethyl, the other must be hydrogen; or the pharmaceutically acceptable cationic salts thereof when A is 5-tetrazolyl or $-CO_2H$.

The various substituent groups disclosed above may be further defined as follows:

(a) Halogen includes chlorine, bromine, fluorine and iodine;

(b) (Lower)alkyl includes both straight and branched chain saturated aliphatic hydrocarbon radicals having from 1 to 6 carbon atoms inclusive, e.g. methyl, ethyl, n-propyl, isopropyl, n-butyl, isobutyl, sec-butyl, t-butyl, n-pentyl, isopentyl, n-hexyl, etc.;

(c) (Lower)alkenyl includes straight or branched unsaturated aliphatic hydrocarbon radicals containing one double bond and having from 2-6 carbon atoms inclusive, e.g. vinyl, allyl, isopropenyl, 2- or 3-methallyl or 3-butenyl;

(d) (Lower)alkynyl represents straight or branched unsaturated aliphatic hydrocarbon radicals containing one triple bond and having from 2 to 6 carbon atoms inclusive, e.g. ethynyl, propargyl, butynyl, pentynyl or hexynyl;

(e) (Lower)alkoxy includes $C_1-C_6$ alkoxy radicals, the alkyl portion of such radicals being defined as in (b) above. Examples include methoxy, ethoxy, n-propoxy, isopropoxy, n-butoxy, isobutoxy, sec-butoxy, n-pentyloxy, isopentyloxy, n-hexyloxy, etc.;

(f) Di(lower)alkoxyethyl represents radicals of the formula $-CH_2CH(O-C_{1-6}\ alkyl)_2$ such as dimethoxyethyl, diethoxyethyl, dipropoxyethyl or dibutoxyethyl;

(g) $C_3-C_6$ Cycloalkyl-$C_1-C_2$ alkyl includes groups such as cyclopropylmethyl, cyclopropylethyl, cyclobutylmethyl, cyclobutylethyl, cyclopentylmethyl or cyclohexylmethyl; and (h) $C_5-C_6$ Cycloalkyl includes cyclopentyl and cyclohexyl.

When substituent A in the compounds of formula I is a tetrazol-5-yl group, those skilled in the art will appreciate that a tautomeric hydrogen atom is present and that the compounds are capable of existing in both forms $I_a$ and $I_a'$ shown below. Both forms may be present to a greater or lesser degree and are in a state of dynamic equilibrium with each other. This invention embraces both forms, but for the sake of convenience, form $I_a$ has arbitrarily been selected to depict the present compounds.

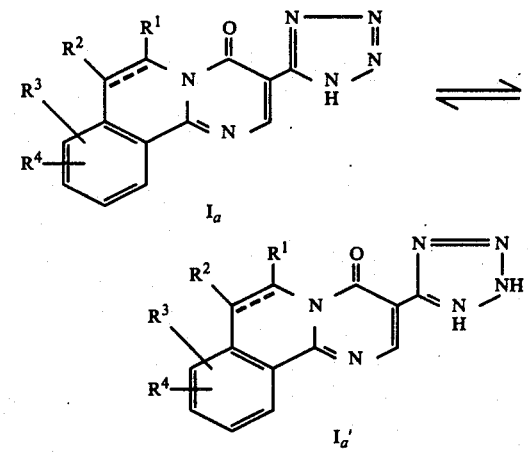

Formula I includes both pyrimido[2,1-a]isoquinoline (double bond between carbon atoms 6 and 7) and the corresponding 6,7-dihydropyrimido[2,1-a]isoquinoline (single bond between C-6 and C-7) derivatives as indicated by the dashed line. The 6,7-dihydro derivatives of formula I where either $R^1$ or $R^2$ is a substituent other than hydrogen contain asymmetric carbon atoms (C-6 and C-7) and, in such cases, the compounds may exist in the form of optical isomers as well as the racemates. All such forms are embraced by the present invention. In the case of the 6,7-dihydro derivatives of formula I where both $R^1$ and $R^2$ are non-hydrogen substituents, the compounds may exist in the form of geometrical isomers. All such isomers are intended to be included in the present invention.

The term "pharmaceutically acceptable cationic salts" is intended to mean non-toxic salts such as the alkali metal salts, e.g sodium and potassium, alkaline earth metal salts such as calcium, magnesium or barium, aluminum salts, ammonium salts and salts with organic bases, e.g. amines such as triethylamine, n-propylamine, tri-n-butylamine, piperidine, ethanolamine, diethanolamine, triethanolamine, diethylaminoethylamine, ethylenediamine, N,N'-dibenzylethylenediamine, benzylamine, tris(hydroxymethyl)aminomethane and pyrrolidine. Salt formation is accomplished by reacting the appropriate carboxylic acid or tetrazole of formula I with a substantially equimolar amount of the appropriate base in an aqueous solution or in a suitable organic solvent such as methanol or ethanol. The salts are recovered by standard methods such as by filtration if they are insoluble in the medium or, if they are soluble in the medium, by evaporation or by precipitation by addition of a non-solvent for the salt.

By "easily cleavable ester group" is meant an ester group removable by methods such as chemical or enzymatic hydrolysis which do not result in any appreciable destruction of the remaining portion of the molecule. Examples are $C_1$-$C_6$ alkyl (preferably ethyl), pivaloyloxymethyl, acetoxymethyl, methoxymethyl, phthalidyl, 1-glyceryl and di(lower)alkylamino(lower)alkyl (preferably diethylaminoethyl). The term "di(lower)alkylamino(lower)alkyl" includes radicals having a total of from 3 to 10 carbon atoms, e.g. dimethylaminomethyl, dimethylaminoethyl, diethylaminomethyl, diethylaminoethyl, dipropylaminomethyl or dibutylaminomethyl. The easily cleavable esters of formula I may find use as pro-drugs in situations where a more prolonged administration of the antiallergy agent is desired.

Substituents $R^3$ and $R^4$ in the compounds of formula I may be located at any of positions 8, 9, 10 and 11 of the pyrimido[2,1-a]isoquinoline ring system and are preferably at positions 9 and 10. Preferred compounds within general formula I are those where $R^1$ is hydrogen and $R^2$ is hydrogen, (lower)alkyl, (lower)alkenyl, hydroxy, (lower)alkoxy, $R^6$—COO— in which $R^6$ is (lower)alkyl or phenyl, di(lower)alkoxyethyl, formylmethyl, phenyl, benzyl, $C_5$-$C_6$ cycloalkyl or $C_3$-$C_6$ cycloalkyl-$C_1$-$C_2$ alkyl.

A preferred embodiment of the present invention comprises the compounds of the formula

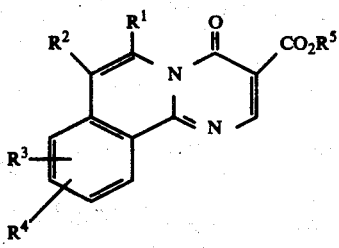

where substituents $R^1$, $R^2$, $R^3$, $R^4$ and $R^5$ are as defined above for compound I, and the pharmaceutically acceptable cationic salts thereof when $R^5$ is hydrogen. Within the group of compounds encompassed by formula I', preferred subgroups are as follows:
(a) The compounds of formula I' wherein $R^5$ is hydrogen;
(b) The compounds of formula I' wherein $R^5$ is (lower)alkyl;
(c) The compounds of formula I' wherein $R^5$ is pivaloyloxymethyl, acetoxymethyl, methoxymethyl, phthalidyl, 1-glyceryl or di(lower)alkylamino(lower)alkyl;
(d) The compounds of formula I' wherein $R^1$ is hydrogen and $R^2$ is hydrogen, (lower)alkyl, (lower)alkenyl, hydroxy, (lower)alkoxy, $R^6$—COO— in which $R^6$ is (lower)alkyl or phenyl, di(lower)alkoxyethyl, formylmethyl, phenyl, benzyl, $C_5$-$C_6$ cycloalkyl or $C_3$-$C_6$ cycloalkyl-$C_1$-$C_2$ alkyl;
(e) The compounds of formula I' wherein substituents $R^3$ and $R^4$ are fixed at ring positions 9 and 10 respectively, and $R^2$, $R^3$ and $R^4$ are as defined in (d); and
(f) The compounds of formula I' wherein substituents $R^3$ and $R^4$ are fixed at ring positions 9 and 10 respectively, $R^1$ is hydrogen, $R^2$ is hydrogen, ethyl, hydroxy, allyl or n-propyl, $R^3$ and $R^4$ are each independently hydrogen or methoxy and $R^5$ is hydrogen or ethyl.

Another preferred embodiment of the present invention comprises the compounds of the formula

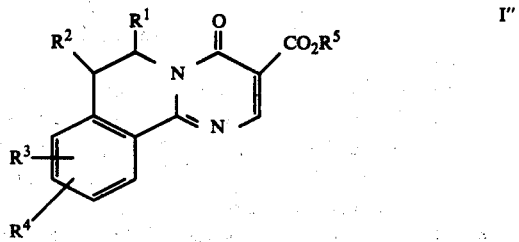

wherein substituents $R^1$, $R^2$, $R^3$, $R^4$ and $R^5$ are as defined above for compound I, and the pharmaceutically acceptable cationic salts thereof when $R^5$ is hydrogen. Within the group of compounds encompassed by formula I", preferred subgroups are as follows:
(a) The compounds of formula I" wherein $R^5$ is hydrogen;
(b) The compounds of formula I" wherein $R^5$ is (lower)alkyl;
(c) The compounds of formula I" wherein $R^5$ is pivaloyloxymethyl, acetoxymethyl, methoxymethyl, phthalidyl, 1-glyceryl or di(lower)alkylamino(lower)alkyl;
(d) The compounds of formula I" wherein $R^1$ is hydrogen and $R^2$ is hydrogen, (lower)alkyl, (lower)alkenyl, hydroxy, (lower)alkoxy, $R^6$—COO— in which $R^6$ is (lower)alkyl or phenyl, di(lower)alkoxyethyl, formylmethyl, phenyl, benzyl, $C_5$-$C_6$ cycloalkyl or $C_3$-$C_6$ cycloalkyl-$C_1$-$C_2$ alkyl;
(e) The compounds of formula I" wherein substituents $R^3$ and $R^4$ are fixed at ring positions 9 and 10 respectively and $R^2$, $R^3$ and $R^4$ are as defined in (d); and
(f) The compounds of formula I" wherein substituents $R^3$ and $R^4$ are fixed at ring positions 9 and 10 respectively, $R^1$ is hydrogen, $R^2$ is hydrogen, ethyl, allyl, formylmethyl or dimethoxyethyl, $R^3$ and $R^4$ are each independently hydrogen, methoxy, hydroxy or isobutyryloxy and $R^5$ is hydrogen or ethyl.

Another preferred embodiment of the present invention comprises the compounds of the formula

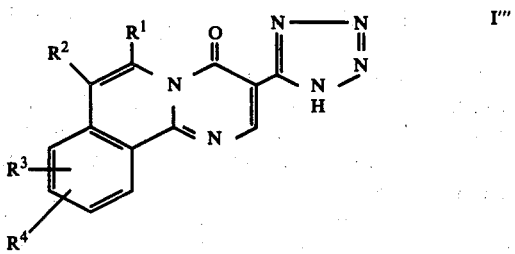

wherein substituents $R^1$, $R^2$, $R^3$ and $R^4$ are as defined above for compound I, and the pharmaceutically acceptable cationic salts thereof. Within the group of compounds encompassed by formula I''', preferred subgroups are as follows:

(a) the compounds of formula I''' wherein $R^1$ is hydrogen and $R^2$ is hydrogen, (lower)alkyl, (lower)alkenyl, hydroxy, (lower)alkoxy, $R^6$—COO— in which $R^6$ is (lower)alkyl or phenyl, di(lower)alkoxyethyl, formylmethyl, phenyl, benzyl, $C_5$-$C_6$ cycloalkyl or $C_3$-$C_6$ cycloalkyl-$C_1$-$C_2$ alkyl;

(b) The compounds of formula I''' wherein substituents $R^3$ and $R^4$ are fixed at ring positions 9 and 10 respectively and $R^2$, $R^3$ and $R^4$ are as defined in (a); and (c) The compounds of formula I''' wherein substituents $R^3$ and $R^4$ are fixed at ring positions 9 and 10 respectively, $R^1$ is hydrogen, $R^2$ is hydrogen, ethyl, hydroxy, allyl or n-propyl and $R^3$ and $R^4$ are each independently hydrogen or methoxy.

Another preferred embodiment of the present invention comprises the compounds of the formula

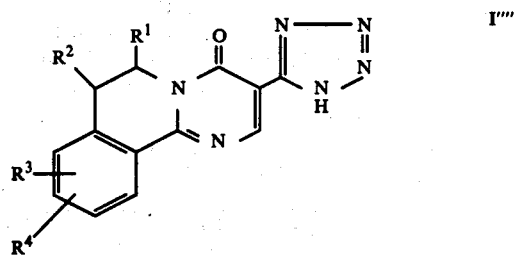

wherein substituents $R^1$, $R^2$, $R^3$ and $R^4$ are as defined above for compound I, and the pharmaceutically acceptable cationic salts thereof. Within the group of compounds encompassed by formula I'''', preferred subgroups are as follows:

(a) The compounds of formula I'''' wherein $R^1$ is hydrogen and $R^2$ is hydrogen, (lower)alkyl, (lower)alkenyl, hydroxy, (lower)alkoxy, $R^6$—COO— in which $R^6$ is (lower)alkyl or phenyl, di(lower)alkoxyethyl, formylmethyl, phenyl, benzyl, $C_5$-$C_6$ cycloalkyl or $C_3$-$C_6$ cycloalkyl-$C_1$-$C_2$ alkyl;

(b) The compounds of formula I'''' wherein substituents $R^3$ and $R^4$ are fixed at ring positions 9 and 10 respectively and $R^2$, $R^3$ and $R^4$ are as defined in (a); and (c) The compounds of formula I'''' wherein substituents $R^3$ and $R^4$ are fixed at ring positions 9 and 10 respectively, $R^1$ is hydrogen, $R^2$ is hydrogen, ethyl, allyl, formylmethyl or dimethoxyethyl and $R^3$ and $R^4$ are each independently hydrogen, methoxy, hydroxy or isobutyryloxy.

The compounds of the present invention may be prepared by the methods set forth below. Unless otherwise stated, substituents $R^1$-$R^5$ referred to in the process description below are as defined above for the compounds of formula I.

Compounds of formula I where A is —$CO_2R^5$ in which $R^5$ is (lower)alkyl may be prepared by condensation of the appropriate 1-aminoisoquinoline or 1-amino-3,4-dihydroisoquinoline starting material of the formula

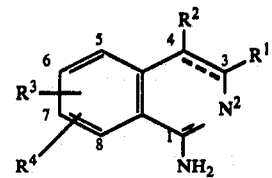

with the appropriate di(lower)alkyl ethoxymethylenemalonate of the formula

$$C_2H_5OCH=C(CO_2\text{-(lower)alkyl})_2 \quad \text{III}$$

in the presence or absence of an inert organic solvent. The condensation is preferably carried out by heating a stoichiometric mixture of reactants II and III.

When a 1-amino-3,4-dihydroisoquinoline starting material is employed, the condensation reaction proceeds directly to the desired 6,7-dihydro-4H-pyrimido[2,1-a]isoquinoline esters of formula I. Reaction temperature is not critical in this case and the condensation may be carried out at room temperature or at elevated temperatures. Advantageously the reactants are heated to about 100° C. to ensure completeness of the reaction. An inert organic solvent (e.g. toluene, benzene or acetonitrile) or mixture of such solvents may be used or, alternatively, the reactants may be mixed neat.

In the case where a 1-aminoisoquinoline starting material is used, the reaction is carried out with heating, preferably at temperatures above about 80° C. An inert organic solvent having a boiling point above the reaction temperature may be employed (e.g. an alcohol or hydrocarbon) or the reactants may be heated neat. Condensation of a 1-aminoisoquinoline produces an intermediate of the formula

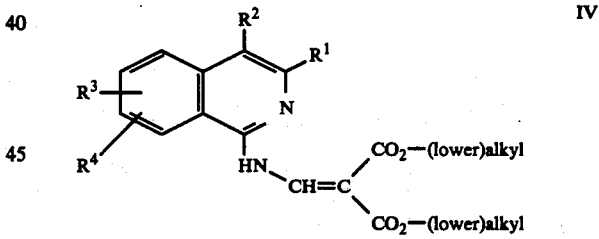

Intermediate IV is then thermally cyclized at elevated temperatures (preferably temperatures in the range of about 200°-260° C.) in a high boiling inert organic solvent such as diphenyl ether, mineral oil, "Dowtherm A" (trademark for a mixture of 26.5% diphenyl and 73.5% diphenyl ether), perhydronaphthalene, diethylbenzene, acetic anhydride containing sulfuric acid or other high boiling hydrocarbons to give the desired ester of formula I. The condensation and cyclization steps may be conducted in a single operation without isolation of intermediate IV by employing a sufficiently high reaction temperature, e.g. 200°-260° C. Alternatively and preferably, however, the reaction is carried out in two steps with intermediate IV being isolated and purified before cyclization.

In employing the condensation reactions described above, the desired (lower)alkyl ester of formula I may be directly prepared by selection of the appropriate dialkyl ethoxymethylenemalonate starting material.

Preferably, however, diethyl ethoxymethylenemalonate is used to give the ethyl ester product which is then converted by known methods to other desired (lower)alkyl esters or to the pivaloyloxymethyl, acetoxymethyl, methoxymethyl, phthalidyl, 1-glyceryl or dialkylaminoalkyl esters. Compounds of formula I where A is —CO₂H may be prepared from the corresponding (lower)alkyl esters by either acidic (e.g. HCl) or basic (e.g. NaOH, KOH) hydrolysis. Acidic hydrolysis, most preferably with a mixture of acetic acid and concentrated hydrochloric acid, is preferred when the 6,7 double bond is present since better yields of the free acids are obtained. The free acid products of formula I may then, if desired, be converted to pharmaceutically acceptable cationic salts by reaction with the appropriate base in a suitable solvent according to known procedures or they may be esterified by known methods to give the desired easily cleavable esters.

The 6,7-dihydropyrimido[2,1-a]isoquinoline products of the formula

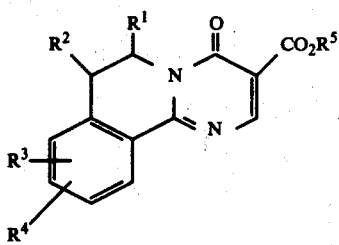

where R⁵ is (lower)alkyl may also be prepared by reduction as by catalytic hydrogenation of the corresponding unsaturated (lower)alkyl ester product of the formula

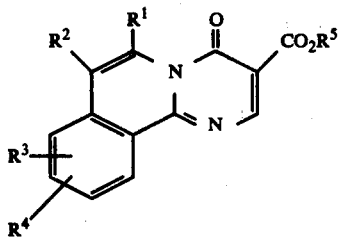

To obtain a formula I" product having R¹-R⁴ substituents identical to those in starting material I', it is of course necessary to exclude R¹-R⁴ substituent groups from compound I' which are readily reducible, e.g. (lower)alkenyl, (lower)alkynyl, formylmethyl and probably halogen. Catalytic hydrogenation may conveniently be carried out by employing a palladium-on-carbon catalyst and acetic acid as the solvent. The esters of formula I" may then be converted as described above to the corresponding free acids or to pharmaceutically acceptable cationic salts or easily cleavable esters of the free acids.

The unsaturated pyrimido[2,1-a]isoquinoline (lower)alkyl esters of formula I (formula I' above) above may also be prepared by dehydrogenation of the corresponding saturated 6,7-dihydropyrimido[2,1-a]isoquinoline ester of formula I". Dehydrogenation may be accomplished by heating ester I" with a dehydrogenating agent such as sulfur, selenium, selenium dioxide, chloranil (tetrachlorobenzoquinone), o-chloranil, 2,3-dichloro-5,6-dicyano-1,4-benzoquinone (DDQ), pyridinium hydrobromide, ceric ammonium nitrate (CAN) or, preferably, palladium-on-carbon in the presence of p-cymene.

Unsaturated pyrimido[2,1-a]isoquinoline carboxylic acids of the formula

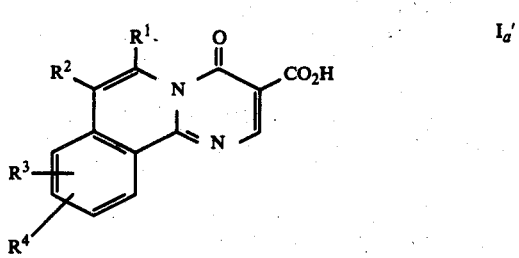

may also be prepared by subjecting the intermediate of the formula

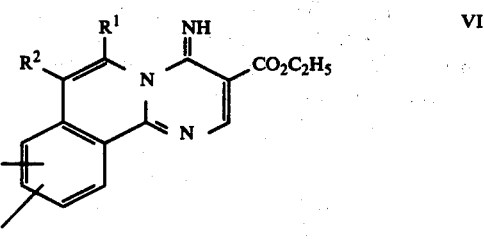

to acid hydrolysis. The nature of the acid used in the hydrolysis is not critical. Good results have been achieved with a mixture of acetic acid and concentrated hydrochloric acid. Following hydrolysis, compound $I_a'$ may, if desired, be converted to a pharmaceutically acceptable cationic salt or an easily cleavable ester.

Compounds of formula I where A is tetrazol-5-yl may be prepared by the methods described below.

Unsaturated pyrimido[2,1-a]isoquinoline tetrazoles of the formula

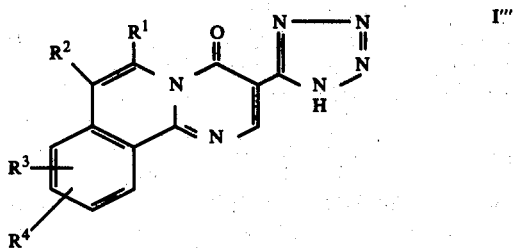

may be readily prepared by the process comprising the steps of (a) condensing the appropriate 1-aminoisoquinoline starting material of the formula

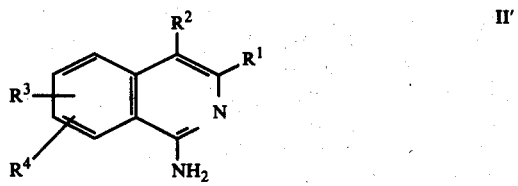

with ethyl ethoxymethylenecyanoacetate in the presence or absence of an inert organic solvent (e.g. toluene) to produce an acrylate intermediate of the formula

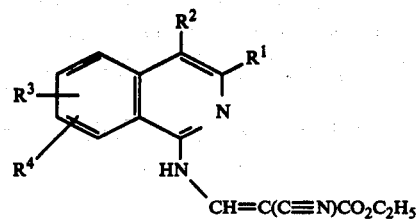

; and (b) reacting intermediate V with aluminum azide in tetrahydrofuran to produce tetrazole I'''.

Condensation step (a) in the above process may be accomplished by reacting approximately equimolar amounts of reactants II' and ethyl ethoxymethylenecyanoacetate. Reaction temperatures can vary from below room temperature (e.g. ~0° C.) to elevated temperatures (e.g. 100° C. or more). Step (a) provides a mixture of the desired acrylate intermediate V and a cyclized imino ester of the formula

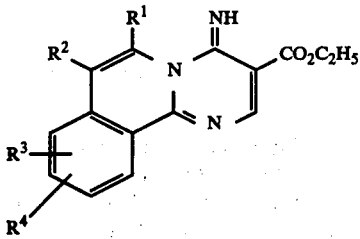

which can be used as described above as an intermediate in the preparation of the unsaturated pyrimido[2,1-a]isoquinoline-3-carboxylic acids of formula $I_a'$. Compounds of formula VI have also been found to possess potent antiallergy activity as illustrated by the rat PCA screening data in Table II below for ethyl 4-imino-4H-pyrimido[2,1-a]isoquinoline-3-carboxylate. The ratio of acrylate V to imino ester VI may be maximized by running condensation step (a) at lower temperatures, i.e. from room temperature down to about 0° C.

Intermediate V is reacted according to step (b) of the process with aluminum azide in tetrahydrofuran to form the desired tetrazole end-product. Approximately equimolar quantities of the reactants are used and the aluminum azide may conveniently be prepared in situ by reaction of sodium azide and aluminum chloride in molar proportions of about 3:1, respectively. While the reaction temperature for step (b) is not critical, advantageous results have been obtained at the reflux temperature of the solvent. Tetrazole product I''' may be easily recovered from the reaction medium by addition of sufficient water followed by acidification to effect precipitation. The tetrazole product produced by this and the following procedures may, if desired, be further converted to a pharmaceutically acceptable cationic salt.

A preferred embodiment comprises the reaction step (b) of preparing tetrazole product I''' from acrylate intermediate V.

Tetrazole products of formula I''' may also be prepared by reaction of a nitrile intermediate of the formula

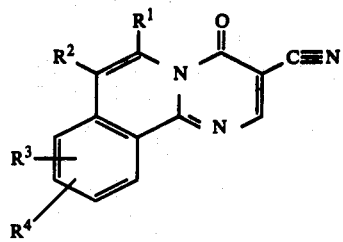

with aluminum azide in tetrahydrofuran. Approximately equimolar quantities of reactants are used and the aluminum azide is preferably formed in situ from sodium azide and aluminum chloride as described in the acrylate V→ tetrazole process above. Reaction temperatures and the tetrazole recovery procedure are as described for the acrylate conversion process.

Saturated 6,7-dihydropyrimido[2,1-a]isoquinoline tetrazoles of the formula

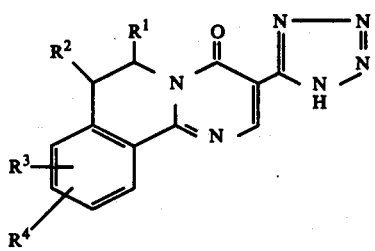

may be prepared by reacting a nitrile intermediate of the formula

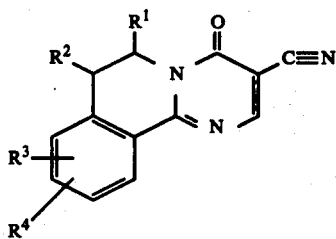

with aluminum azide in tetrahydrofuran or with an azide salt selected from the group consisting of ammonium azide, substituted ammonium azide, sodium azide and lithium azide in an inert organic solvent. Nitrile VII and the azide salt are preferably employed in approximately equimolar amounts. The general conversion of nitriles to tetrazoles is described by W. G. Finnegan, et al. in *J. Am. Chem. Soc.*, 80, 3908 (1958). Examples of suitable azide salts for this process are provided by Finnegan in the above-mentioned reference and include azides such as $NaN_3$, $LiN_3$, $NH_4N_3$, $(n\text{-}C_4H_9)_2NH_2N_3$, $C_6H_5NH_3N_3$ and $(CH_3)_4NN_3$. The azide salt may be added directly or may be generated in situ, e.g. by double decomposition reactions of sodium azide and an appropriate chloride salt such as $LiCl$, $AlCl_3$, $NH_4Cl$, $(CH_3)_4NCl$, etc. While the condensation reaction proceeds over a wide temperature range, it is preferred in order to minimize reaction times to use elevated temperatures, e.g. from about 100° C. up to the reflux temperature of the solvent system. The inert organic solvent may in general be any solvent having good solvent power for the azide salt and which is chemically inert.

Examples of preferred solvents are dimethylformamide, dimethylacetamide, dimethylsulfoxide and hexamethylphosphoramide. The most preferred solvent is dimethylformamide. The condensation reaction is found to be subject to general acid catalysis and yields are improved by addition of such reagents as hydrazoic acid, amine hydroazides and Lewis acids such as $BF_3$ to the sodium azide. At the completion of the reaction, the tetrazole product may be recovered from the reaction mixture by removing the solvent, diluting the residue with water and then acidifying the mixture to give the desired product of formula I''''.

The nitrile starting materials of formulae VII and VII' may be conveniently prepared from the 6,7-dihydropyrimido[2,1-a]isoquinoline esters of formula I'' by the route indicated below:

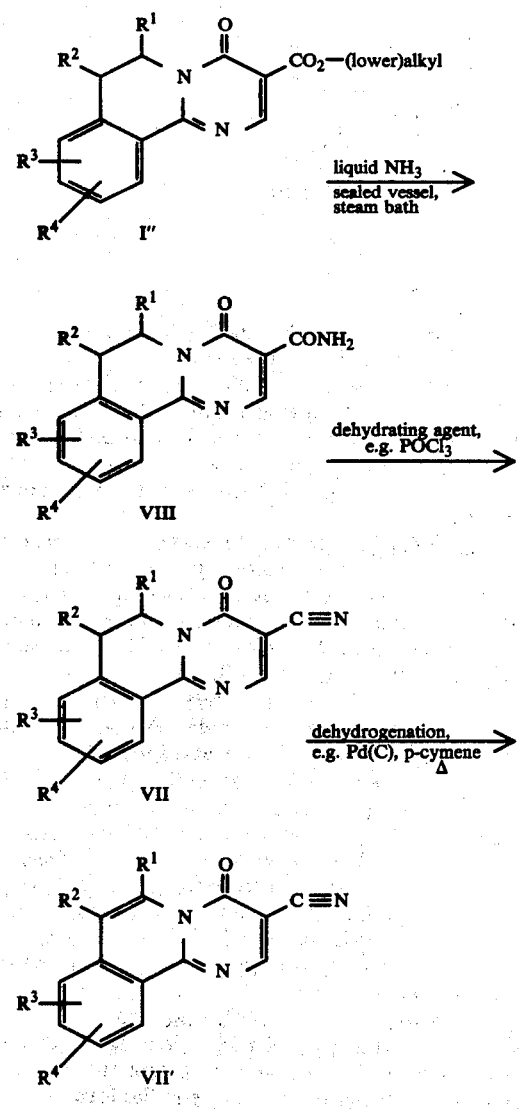

Amides of formula VIII may be obtained by treatment of the esters of formula I'' with liquid ammonia, ammonium hydroxide or a solution of ammonia in a (lower)alkanol (e.g. methanol or ethanol) optionally containing sodium methoxide as a catalyst. The reaction is conveniently carried out in a sealed vessel at steam bath temperature.

The amide intermediates may be converted to nitriles of formula VII by use of a dehydrating agent such as phosphorus pentoxide, thionyl chloride, p-toluenesulfonyl chloride:pyridine or, most preferably, phosphorus oxychloride. Dehydration is accomplished at elevated temperatures, most preferably under reflux conditions.

Nitrile VII may be converted to the corresponding unsaturated nitrile VII' by dehydrogenation at elevated temperatures with a dehydrogenating agent such as described above for conversion of compounds I'' to compounds I'. A preferred procedure involves heating nitrile VII with palladium-on-carbon in the presence of p-cymene. As described above, nitrile VII' may be used as a starting material in the preparation of tetrazole I'''.

Compounds of formula I prepared by any of the above methods may, if desired, be further reacted by methods known per se to convert one or more $R^1$, $R^2$, $R^3$ or $R^4$ substituents to other substituent groups within the scope of formula I. Thus, for example, a (lower)alkoxy-substituted product may be subjected to acid hydrolysis (e.g. HCl or HCl-HOAc) to provide the corresponding hydroxy-substituted product. This product may then in turn be realkylated, e.g. with an alkyl halide in the presence of a base, to give a (lower)alkoxy-substituted product, preferably one having a (lower)alkoxy substituent different from that in the starting product. Acylation of a hydroxy-substituted product with the appropriate benzoyl halide or (lower)alkanoyl halide gives the corresponding benzoyl- or (lower)alkanoyloxy-substituted compound. Ozonolysis of the allyl-substituted product gives the formylmethyl-substituted compound which can in turn be reduced to the hydroxyethyl-substituted product. The allyl-substituted compound can also be hydrated to give the corresponding hydroxypropyl product. Compounds having a dialkoxyethyl substituent may be prepared by treating the corresponding formylmethyl-substituted compound with the appropriate (lower)alkanol, e.g. methanol gives dimethoxyethyl, ethanol gives diethoxyethyl, etc.

The 1-aminoisoquinoline and 1-amino-3,4-dihydroisoquinoline starting materials used in the above process are known in the art or are prepared by known methods.

One procedure for preparing 1-amino-3,4-dihydroisoquinolines is illustrated in the following reaction scheme:

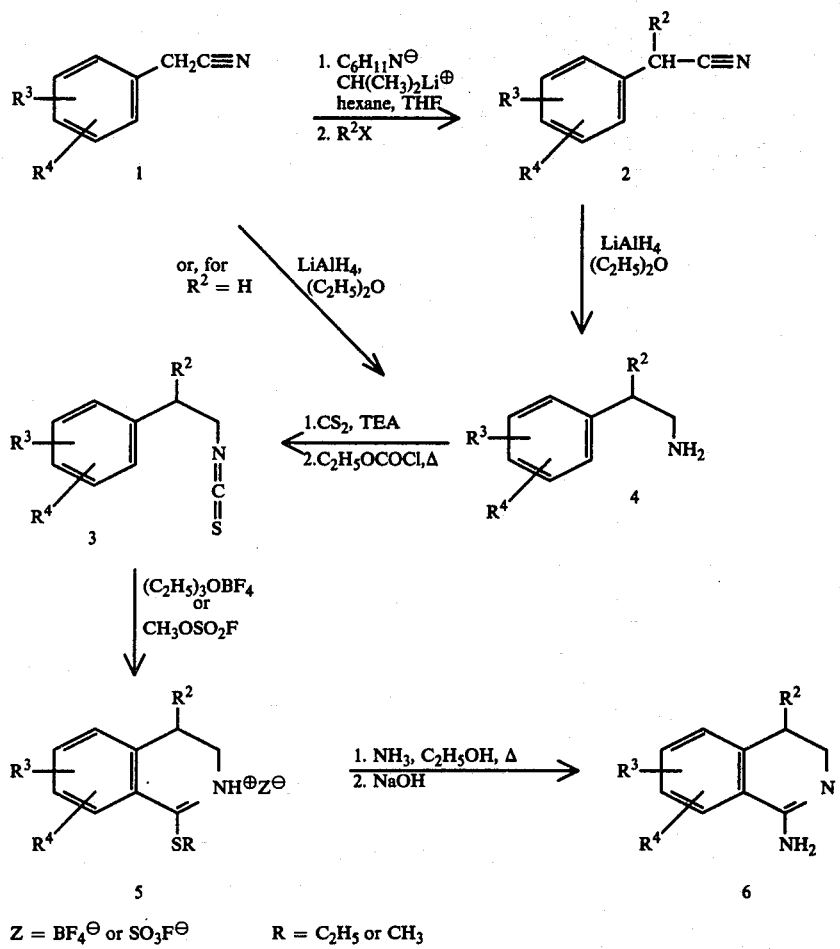

Z = BF$_4^\ominus$ or SO$_3$F$^\ominus$    R = C$_2$H$_5$ or CH$_3$

Alkylation of the phenylacetonitriles 1 can be carried out using various conventional bases such as sodamide or sodium hydride, but almost quantitative yields have been obtained by use of the lithium salt of N-isopropylcyclohexylamine. Reduction of the phenylacetonitriles (1 or 2) to give the phenethylamines 4 and formation of the isothiocyanates 3 from the latter are well-known reactions. Cyclization of the isothiocyanates 3 to the isoquinolinium salts 5 occurs using very mild conditions, permitting a wide variety of substituents to be introduced on the isoquinoline nucleus. This general method has been described in J. Chem. Soc., Perkin Trans. 1, 1, 33 (1976). Reaction of the isoquinolinium salts 5 in a steel bomb at about 100° C. with ethanol which has been saturated with ammonia gives either the fluoroborate salt or the fluorosulfonate salt of 6. Treatment of the salts with sodium hydroxide liberates the free bases 6.

The 1-aminoisoquinoline starting materials may be prepared from the corresponding 1-amino-3,4-dihydroisoquinolines by dehydrogenation as by treatment with palladium-on-carbon in boiling p-cymene.

Use of the Chichibabin reaction (J. Russ. Phys. Chem. Soc., 50, 543 (1920) and U.S. Patent 3,847,919) on the requisite isoquinolines provides another route to the 1-aminoisoquinolines. Pesson and Richer [French Pat. No. 3589M and Compt. rend., Ser. C., 262 (24), 1719 (1966)] disclose preparation of 1-aminoisoquinolines by reduction of the corresponding 1-hydrazino compounds.

In another aspect the present invention provides a method of inhibiting or preventing the symptoms of an allergic reaction such as allergic bronchial asthma or allergic rhinitis in a mammal susceptible to such a reaction which comprises administering to said mammal a prophylactically effective dose of a compound of formula I or a pharmaceutically acceptable cationic salt thereof.

In yet another aspect the present invention provides a pharmaceutical composition, useful as an antiallergy agent, which comprises, as the active ingredient, a compound of formula I or a pharmaceutically acceptable cationic salt thereof, in admixture with a pharmaceutically acceptable carrier or diluent.

The compounds of the present invention may be administered either as individual therapeutic agents or as mixtures with other therapeutic agents. They may be administered alone but are generally given in the form of pharmaceutical compositions. Examples of such compositions include tablets, lozenges, capsules, powders, aerosol sprays, aqueous or oily suspensions, ointments, syrups, elixers and aqueous solutions. The compounds are preferably administered orally, but may also be given by inhalation, injection, instillation or by implantation for controlled drug release from a solid carrier reservoir.

The nature of the pharmaceutical composition and the pharmaceutical carrier or diluent will, of course, depend on the desired route of administration. For example, oral compositions may be in the form of tablets or capsules and may contain conventional excipients such as binding agents (e.g. syrup, acacia, gelatin, sorbitol, tragacanth or polyvinylpyrrolidone), fillers, (e.g. lactose, sugar, maize-starch, calcium phosphate, sorbitol or glycine), lubricants (e.g. magnesium stearate, talc, polyethylene glycol, or silica), disintegrants (e.g. starch) or wetting agents (e.g. sodium lauryl sulfate). Oral liquid preparations may be in the form of aqueous or oily suspensions, solutions, emulsions, syrups, elixers, etc. or may be presented as a dry product for reconstitution with water or other suitable vehicle before use. Such liquid preparations may contain conventional additives such as suspending agents, flavoring agents, diluents or emulsifying agents. Topical preparations may be in the form of ointments, both hydrophilic and hydrophobic, in the form of lotions which may be aqueous, non-aqueous or of the emulsion type or in the form of creams. Pharmaceutical carriers useful in the preparation of such formulations will include, for example, such substances as water, oils, greases, polyesters, polyols and the like. For parenteral administration, inhalation or instillation, solutions or suspensions of a compound of formula I with conventional pharmaceutical vehicles may be employed, e.g. as an aerosol spray for inhalation, as an aqueous solution for intravenous injection or instillation, or as an oily suspension for intramuscular injection. The compounds may also be administered by means of inhalers or other devices which permit the active compounds in the form of dry powders to come into direct contact with the lungs.

The compounds of the present invention or pharmaceutical compositions thereof may be administered to human allergic patients in single oral doses of approximately 0.5–500 mg. of active ingredient and multiple oral doses totalling up to about 1000 mg./day of active ingredient. When administered by inhalation of instillation, lower doses are generally given, i.e. on the order of about 0.1 of the normal oral dosage for the particular compound in question. These values are illustrative only, however, and the physician of course will ultimately determine the dosage most suitable for a particular patient on the basis of factors such as age, weight, severity of the symptoms and the particular agent to be administered.

The in vivo animal model studies described below indicate that the compounds of formula I are highly potent antiallergy agents.

Biological Activity Data

The reagin-mediated rat Passive Cutaneous Anaphylaxis (PCA) screening test used to evaluate the present compounds is generally regarded as one of the best animal models for use in predicting the antiallergy activity of test compounds in man. Briefly, the method consists of passive sensitization of skin sites on the test animals with reaginic antibodies followed after 24 hours by administration of the test drug and antigen challenge. The allergic response is measured by use of Evans' blue dye and is evaluated by the spot diameter at the injection side. Details of the test are provided below.

Materials

Ovalbumin (5 times crystalline)
Dinitrobenzene sulfonic acid, Na$^+$ salt
*Bordetella pertussis* vaccine — phase I
10–20 × 10$^9$ killed organisms/ml.
Aluminum hydroxide gel — 10 mg./ml.
Potassium carbonate Male Sprague-Dawley Rats — 200 gms.
Female Sprague-Dawley Rate — 100 gms.
Tris Buffered Saline (TBS) — 0.02 M 2-amino-2-hydroxymethyl-1,3-propanediol (Tris), 0.15 M NaCl, pH 8.2.

Antigen Preparation — DNP-d EA

A substituted ovalbumin antigen is used both as immunogen and challenging antigen. The antigen is prepared as follows: 500 mg. ovalbumin (EA) and 500 mg. $K_2CO_3$ are dissolved in 25 ml. distilled $H_2O$ and stirred at room temperature for 5 minutes. Five hundred (500) mg. dinitrobenzene sulfonic acid, Na$^+$ salt, (previously recrystallized from hot absolute ethanol) is then added slowly with continued stirring. The reaction mixture is then immediately placed in the dark and allowed to proceed for 2 hours with constant stirring. After 2 hours the mixture is placed in suitable dialysis tubing and dialyzed against 5 changes (4 liters each) of distilled $H_2O$ at 5° C. After dialysis the product is lyophilized and stored at room temperature in a brown or amber container. The antigen obtained will appear as a light yellow, amorphous solid which is very soluble in water or saline. It is designated as DNP denatured ovalbumin (DNP-d EA).

Immunization Method for IgE Production

Adult, male Sprague-Dawley rats are used as a source or reagin-rich antisera for the PCA model. Immunization is by a combination of DNP-d EA on Al(OH)$_3$ gel and *B. pertussis* vaccine. Preparation of the DNP-d EA - gel immunogen is as follows: Dissolve the DNP-d EA in TBS so as to give a concentration of 10 mg./ml. Slowly add 1 ml. of this solution to 10 ml. Al(OH)$_3$ gel (10 mg. solids/ml.) with constant stirring at room temperature. Stir the mixture an additional 30 minutes to insure a uniform adsorption of antigen on gel.

The resulting preparation is then used in combination with phase I *B. pertussis* vaccine to immunize male S/D rats as follows: For each rat administer 0.1 ml. DNP-d EA - gel suspension intramuscularly in each hind leg (200 μg DNP-d EA and 2 mg. gel total dose). Follow these injections by the intraperitoneal administration of 1.0 ml. *B. pertussis* vaccine (10–20 × 10$^9$ organisms). The use of light ether anesthesia during this procedure is recommended to insure proper intramuscular and intraperitoneal injections. Nine days following immunization (but no longer than 10) the animals are exsanguinated by cardiac puncture or abdominal aorta cannulation under ether or pentobarbital anesthesia. The collected whole blood is allowed to clot, the serum separated by centrifugation and the individual serum samples stored frozen until assayed for IgE content.

Selection of High Titered Serum Samples for Pooling

Individual serum samples should be screened for reaginic antibody concentration before being pooled with other sera, as not all rats respond to immunization procedures with reagin production. A 1:50 saline dilution of serum from each immunized rat is used for this purpose. Intradermal injections of 0.05 ml. of the diluted sera are made in the shaven backs of two small female recipient rats, 100–120 gms. Several serum samples can be tested simultaneously in recipient animals. After a 24 to 48 hour latent period antigen challenge is accomplished by intravenous administration to each rat of 1 mg. DNP-d EA in 0.5 ml. 0.5% Evans' blue dye in saline. Sera which show positive PCA reactions at the 1:50 dilution, as measured 20 to 30 minutes post-challenge are pooled, dispensed in small aliquots and stored at −70° C. or lower until used. Negative sera may be discarded.

The IgE titer of the antisera pool should then be determined. Serial two-fold dilutions (1:5 to 1:160) of unheated sera and sera heated at 56° C. for 1 hour are prepared in saline and 0.05 ml. of each dilution injected intradermally on the backs of female recipient rats. At least four animals should be used for both the heated and unheated serum titrations. After a 24-hour latent period each group is challenged with 1 mg. DNP-d EA in 0.5 ml. 0.5% Evans' blue dye. Reactions are read by reflecting the skin 20 to 30 minutes post-challenge. Intensity (blueing) and spot diameter should be measured and recorded. The pool titer is defined as the reciprocal of the greatest dilution of unheated serum which yields a measurable PCA response (>6 mm. diameter) in at least half of the recipient animals. Antiserum pools having a titer of 50 or greater are acceptable for the PCA screen. These pools should be sterile-filtered and stored at −70° C. or lower until use. Lyophilization in small aliquots may be used as an alternate.

PCA Screening Method

1. Animals — Young female Sprague-Dawley rats, 90–110 gms. should be used. The rats should be conditioned (acclimatized) for at least five days prior to use, with food and waste ad lib.

2. Passive Sensitization — The test animals are prepared for passive sensitization by carefully shaving areas on each side of the back with a fine toothed clipper. Using a 27 gauge ⅝″ needle mounted on a 1 ml. tuberculin syringe make intradermal injections of saline dilutions of the antiserum pool. Four dilutions (two on either side) of antiserum are used. The exact dilutions used depend on the titer of the pool. For example, if the antiserum pool has a titer of 50, then dilutions of 1:10, 1:20, 1:30 and 1:40 are used; if the pool titers at 100, then the dilutions would be 1:20, 1:40, 1:60 and 1:80. The sequence of placement of each dilution should be either clockwise or counter-clockwise to facilitate ease in scoring. The latent period should be at least 24 but no more than 48 hours.

3. Drug Administration-Standard and Unknowns— Four animals are used for each test compound. Disodium cromoglycate (DSCG), solubilized in saline, is administered by intravenous (i.v.) route at the time of antigen challenge. The test compounds are solubilized in aqueous sodium bicarbonate when possible. Compounds insoluble in bicarbonate are suspended in Tween/CMC. The test compounds are administered i.v. or per os either 1–5 or 10 minutes, respectively, prior to antigen challenge.

4. Anitgen Challenge and Reaction Evaluation — Elicitation of the PCA response is accomplished by intravenous administration of 1 mg. DNP-d EA in 0.5 ml. 0.5% Evans' blue dye in saline to each test rat. PCA reactions are maximal twenty to thirty minutes post-challenge. Reactions should be scored visually for color intensity and the average diameter of the spots measured at each antiserum dilution site. Both operations should be done by reflecting the skin. For comparative purposes the numbers in the control group (untreated) should be at least 5% and usually 10%, of the total animals tested on a particular day.

Observed drug inhibition is reported as percent reduction in effective antiserum titer in treated versus control groups.

Results

Test results for a representative sample of the compounds of the present invention by i.v. and p.o. routes of administration are shown below in Tables I and II along with data for disodium cromoglycate (DSCG). The results are given in terms of the $ID_{50}$ value, i.e. the dose of compound that inhibits 50% of the response.

Table 1

6,7-Dihydropyrimido[2,1-a]isoquinolines

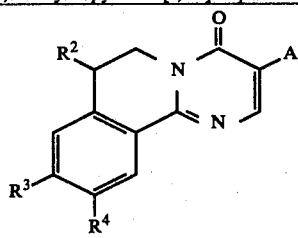

| Example No. | $R^2$ | $R^3$ | $R^4$ | A | Rat PCA Test $ID_{50}$, mg./kg. p.o. |
|---|---|---|---|---|---|
| 6 | H | H | H | $CO_2Et$ | 2.3 |
| 7 | H | H | H | $CO_2H$ | 7.9 |
| 9 | H | OMe | H | $CO_2Et$ | ~13 |
| 11A | H | OMe | H | $CO_2H$ | 2.6 |
| 10A | H | H | OMe | $CO_2Et$ | ~0.81 |
| 11B | H | H | OMe | $CO_2H$ | ~0.48 |
| 19 | H | H | OH | $CO_2H$ | ~1.2 |
| 21 | H | H | $-OCOCH(Me)_2$ | $CO_2H$ | ~0.5 |
| 10B | Et | H | H | $CO_2Et$ | 0.13 |
| 11C | Et | H | H | $CO_2H$ | 0.048 |
| 23 | Et | H | H | $CHN_4$ | 0.10 |
| 10C | H | OMe | OMe | $CO_2Et$ | ~0.37 |
| 11D | H | OMe | OMe | $CO_2H$ | ~0.31 |
| 24 | H | OMe | OMe | $CHN_4$ | ~0.030 |
| 20 | H | OH | OH | $CO_2H$ | ~0.077 |
| 10D | $-CH_2CH=CH_2$ | H | OMe | $CO_2Et$ | ~0.31 |
| 11E | $-CH_2CH=CH_2$ | H | OMe | $CO_2H$ | ~0.077 |
| 22 | $-CH_2CHO$ | H | OMe | $CO_2Et$ | ~20 |
| 22 | $-CH_2CH(OMe)_2$ | H | OMe | $CO_2Et$ | ~3.3 |

Table 1-continued 6,7-Dihydropyrimido[2,1-a]isoquinolines

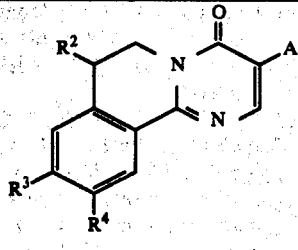

| Example No. | $R^2$ | $R^3$ | $R^4$ | A | Rat PCA Test $ID_{50}$, mg./kg. p.o. |
|---|---|---|---|---|---|
| DSCG | | | | | >>30 |

In the table above the following abbreviations are used; Et = $C_2H_5$; Me = $CH_3$; $CHN_4$ = 1H-tetrazol-5-yl.
In the case of DSCG, the compound was dosed 30 minutes prior to challenge.
The i.v. $ID_{50}$ dose of DSCG was found to be 0.6 mg./kg.

Table II

Pyrimido[2,1-a]isoquinolines

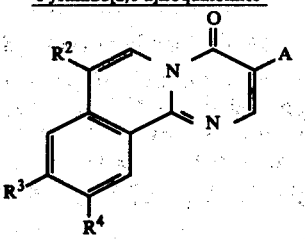

| Ex. No. | $R^2$ | $R^3$ | $R^4$ | A | Rat PCA Test $ID_{50}$, mg./kg. i.v. | p.o. |
|---|---|---|---|---|---|---|
| 1 | H | H | H | $CO_2Et$ | | >>5 |
| 2,3 | H | H | H | $CO_2H$ | | 0.33 |
| 8 | H | H | H | $CHN_4$ | | 0.04 |
| 12 | H | OMe | H | $CO_2Et$ | | ~31 |
| 18 | H | OMe | H | $CO_2H$ | | ~1.5 |
| 13A | H | H | OMe | $CO_2Et$ | | ~0.9 |
| 16 | H | H | OMe | $CO_2H$ | | ~1.0 |
| 13B | Et | H | H | $CO_2Et$ | | ~5.0 |
| 17A | Et | H | H | $CO_2H$ | | ~0.048 |
| 25 | Et | H | H | $CHN_4$ | 0.009 | 0.04 |
| 5 | OH | H | H | $CO_2H$ | | ~1.7 |
| 13C | H | OMe | OMe | $CO_2Et$ | | ~2.63 |
| 17B | H | OMe | OMe | $CO_2H$ | | ~0.01 |
| 14 | —$CH_2CH=CH_2$ | H | OMe | $CO_2Et$ | | >5.0 |
| 17C | —$CH_2CH=CH_2$ | H | OMe | $CO_2H$ | | ~0.53 |
| 15 | —$CH_2CH_2CH_3$ | H | OMe | $CO_2Et$ | | ~16 |
| 17D | —$CH_2CH_2CH_3$ | H | OMe | $CO_2H$ | | ~0.071 |
| DSCG | | | | | 0.6 | >>30 |

In the table above the following abbreviations are used: Et = $C_2H_5$, Me = $CH_3$; $CHN_4$ = 1H-tetrazol-5-yl.
In addition to the above, the compound ethyl 4-imino-4H-pyrimido-[2,1-a]isoquinoline-3-carboxylate prepared in Example 3A below was tested and found to have a p.o. $ID_{50}$ of ~0.19 mg./kg.

The following examples are provided solely for the purpose of illustrating preparation of the starting materials and end-products of the present invention and are not to be construed as limitations of the invention. All temperatures referred to below are in degrees Centigrade. Melting and boiling points are uncorrected. "Skellysolve B" is the trademark of Skelly Oil Co. for a petroleum ether fraction of b.p. 60°–68° C. consisting essentially of n-hexane.

Preparation of Starting Materials

A. 1-Amino-3,4-dihydroisoquinolines (a) Phenylacetonitriles (structure 2)

1. (±)-2-Allyl-2-(4-methoxyphenyl)acetonitrile n-Butyl lithium (0.16 mole of 1.6 M in hexane) was added under a nitrogen atmosphere to dry tetrahydrofuran (100 ml.) which was cooled in a $CO_2$-acetone bath. This was followed by the successive dropwise additions during 10 minutes of solutions in tetrahydrofuran (10 ml. each) of N-isopropylcyclohexylamine (22.6 g., 0.160 mole) and p-methoxyphenylacetonitrile (21.2 g., 0.144 mole). The mixture was stirred in the cold for 10 minutes when allyl bromide (24.2 g., 0.20 mole) was added dropwise during 10 minutes. Stirring was continued in the cold for 15 minutes and then at ambient temperature for 1.5 hours. The solution was diluted with diethyl ether and washed successively with 4% hydrochloric acid (2 × 100 ml.) $H_2O$ and brine. The ethereal solution was dried ($Na_2SO_4$), concentrated, and the residue distilled to give 24.2 g. (89% yield) of the nitrile, b.p. 99°–114° (0.1 mm.).

2. (±)-2-Phenylbutyronitrile

Using the method of Procedure A.(a) 1, alkylation of phenylacetonitrile with ethyl bromide gave a 98% yield of the title compound, b.p. 110°–116° at 13 mm. (Lit.[1] b.p. 124°–126° at 25 mm.).
[1] Compt. rend., 232, 1424 (1951).

(b) Phenethylamines (structure 4)

1. (±)-2-Allyl-2-(4-methoxyphenyl)ethylamine

A solution of (±)-2-allyl-2-(4-methoxyphenyl)acetonitrile (159.7 g., 0.852 mole) in diethyl ether (200 ml.) was added dropwise during 20 minutes to a stirred, slowly refluxing mixture of lithium aluminum hydride ($LiAlH_4$, 42.2 g., 1.11 moles) in diethyl ether (800 ml.). The mixture was refluxed for an additional 1.25 hours and then cooled in an ice-$H_2O$ bath. The excess $LiAlH_4$ was decomposed by the slow dropwise addition of $H_2O$ until gaseous evolution ceased, and a granular precipitate formed. The mixture was filtered and the filter cake thoroughly washed with diethyl ether. Concentration of the filtrate gave the title product (146 g., 90%) as a cloudy oil.

A sample of the oil was distilled to give product b.p. 78°–84° (0.1 mm.) which was characterized as the hydrogen fumarate salt, m.p. 137°–139° after recrystallization from ethanol-ether.

Anal. Calcd for $C_{12}H_{17}NO.C_4H_4O_4$: C, 62.52; H, 6.88; N, 4.56. Found: C, 62.05; H, 7.22; N, 4.50.

2. 2-(4-Methoxyphenyl)ethylamine and (±)-2-phenylbutylamine

In a similar manner to the preparation of (±)-2-allyl-2-(4-methoxyphenyl)ethylamine described above, reduction of p-methoxyphenylacetonitrile and (±)-2-phenylbutyronitrile with lithium aluminum hydride provided 2-(4-methoxyphenyl) ethylamine[2] and (±)-2-phenylbutylamine,[3] respectively.

[2] Ber., 42, 4778 (1909).
[3] Compt. rend., 184, 30 (1927).

(c) Arylalkyl Isothiocyanates (structure 3)

Starting from the appropriate arylalkylamines, the procedure described by Gittos et al.,[4] was used to synthesize the following isothiocyanates: 2-(4-methoxyphenyl)ethyl isothiocyanate (100% yield), b.p. 112°–114° at 0.1 mm. (Lit.[5] b.p. 119°–120° at 0.5 mm.); 2-(3-methoxyphenyl)ethyl isothiocyanate (89% yield), b.p. 135°–140° at 0.1 mm.; 2-(3,4-dimethoxyphenyl)ethyl isothiocyanate (52% yield, b.p. 155°–165° at 0.4 mm. (Lit.[4] b.p. 138°–140° at 0.2 mm.); (±)-2-phenylbutyl isothiocyanate (97% yield), b.p. 85°–98° at 0.1 mm.; and (±)-2-allyl-2-(4-methoxyphenyl)ethyl isothiocyanate (81% yield), b.p. 136°–144° at 0.1 mm.

[4] J. Chem. Soc., Perkin Trans. 1, 1, 33 (1976).
[5] U.K. Pat. No. 1,141,586

(d) 1-Ethylthio- and 1-Methylthioisoquinolinium Salts (structure 5)

The processes and procedures of Gittos[6] and Gittos et al.,[4] were used to cyclize the preceding isothiocyanates to the following isoquinolinium salts: 1-ethylthio-3,4-dihydro-6,7-dimethoxyisoquinolinium fluoroborate (79% yield), m.p. 175°–177° from ethanol-ether (Lit.[4] m.p. 174°–176°); 3,4-dihydro-7-methoxy-1-methylthioisoquinolinium fluorosulfonate (41% yield), m.p. 208°–209.5° from acetonitrile (Anal. Calcd for $C_{11}H_{13}NOS \cdot HSO_3F$: C, 42.99; H, 4.59; N, 4.56; S, 20.86. Found: C, 43.41; H, 4.93; N, 4.53; S, 20.99;

3,4-dihydro-6-methoxy-1-methylthioisoquinolinium fluorosulfonate (100% crude yield), m.p. 106°–119° from methylene chloride-ether; (±)-4-ethyl-3,4-dihydro-1-methylthioisoquinolinium fluorosulfonate and (±)-4-allyl-3,4-dihydro-7-methoxy-1-methylthioisoquinolinium fluorosulfonate were isolated as gummy oils which were used without purification.

[6] U.S. Pat. No. 3,895,014
[4] J. Chem. Soc., Perkin Trans. 1, 1, 33 (1976).

(e) 1-Amino-3,4-dihydroisoquinolines (structure 6)

3,4-Dihydro-7-methoxy-1-methylthioisoquinolinium fluorosulfonate (10.0 g., 0.0362 mole) was added to ethanol (100 ml.) which was saturated with ammonia in a steel bomb. The stirred mixture was heated on a steam bath for 2 hours. The mixture was combined with material from four similar runs andd flash evaporated to dryness. The residue was partitioned between 5N NaOH (300 ml.) and methylene chloride. The organic layer was washed with water (2×) and dried with sodium sulfate. The solid obtained after removal of the methylene chloride was recrystallized from benzene to give 23 g. (72% yield) of 1-amino-3,4-dihydro-7-methoxyisoquinoline, m.p. 114°–117.5°. Recrystallization from ethyl acetate afforded the analytical sample, m.p. 117.5°–119.5°.

Anal. Calcd for $C_{10}H_{12}N_2O$: C, 68.16; H, 6.86; N, 15.90. Found: C, 68.01; H, 6.81; N, 15.83.

The following 1-amino-3,4-dihydroisoquinolines were prepared similarly: 1-amino-3,4-dihydro-6,7-dimethoxyisoquinoline[7] (105% crude yield, fluoroborate salt had m.p. 181°–185° from ethanol); 1-amino-3,4-dihydro-6-methoxyisoquinoline (41% yield), m.p. 129°–131° from ethyl acetate (Anal. Calcd. for $C_{10}H_{12}N_2O$: C, 68.16; H, 6.86; N, 15.90. Found: C, 68.39; H, 7.01; N, 16.05);

(±)-1-amino-4-ethyl-3,4-dihydroisoquinoline (102% crude yield of brown oil), characterized as the monohydrogen fumarate salt, m.p. 146°–148° from water (Anal. Calcd for $C_{11}H_{14}N_2 \cdot C_4H_4O_4$: C, 62.05; H, 6.25; N, 9.65. Found: C, 60.95; H, 6.12; N, 9.26); and (±)-4-allyl-1-amino-3,4-dihydro-7-methoxyisoquinoline, a brown oil, after isolation as, and regeneration from the monohydrogen fumarate salt, m.p. 174°–176° from ethanol.

[7] Yakugaku Zasshi, 82, 352 (1962).

(Anal. Calcd for $C_{13}H_{16}N_2O \cdot C_4H_4O_4$: C, 61.43; H, 6.07; N, 8.43. Found: C, 60.82; H, 6.15; N, 7.82).

B. 1-Aminoisoquinolines

1. 1-Amino-4-methoxyisoquinoline

Reduction of 1-hydrazino-4-methoxyisoquinoline[8] with hydrogen and Raney Ni in ethanol according to the procedure of Pesson and Richer[8] have a 17% yield of the title compound, m.p. 112.5–114° after chromatography on alumina with chloroform-ethanol (20:1).

[8] Compt. rend., Ser. C, 262 (24), 1719 (1966).

2. 1-Amino-4-ethylisoquinoline

A stirred mixture of (±)-1-amino-4-ethyl-3,4-dihydroisoquinoline (6.83 g.) and 10% palladium on carbon (1.5 g.) in p-cymene (80 ml.) was refluxed for 4 hours. The mixture was filtered and the filtrate reduced to dryness in vacuo to leave an oil which when crystallized successively from Skellysolve B and cyclohexane gave 1.84 g. (27% yield) of the product, m.p. 84°–85°.

Anal. Calcd for $C_{11}H_{12}N_2$: C, 76.71; H, 7.02; N, 16.27. Found: C, 76.87; H, 6.98; N, 16.15.

EXAMPLE 1

Ethyl 4-Oxo-4H-pyrimido[2,1-a]isoquinoline-3-carboxylate (via intermediate IV)

A. Diethyl Isoquinolylaminomethylenemalonate

A stirred mixture of 1-aminoisoquinoline (20.0 g., 0.139 mole) and diethyl ethoxymethylenemalonate (30.0 g., 0.139 mole) was heated at an oil bath temperature of 105° under a nitrogen atmosphere for 10 minutes. Dilution of the warm, vigorously stirred reaction mixture with Skellysolve B (150 ml.) resulted in crystallization of product (41.8 g., 92.7% yield) with m.p. 61°–65°. Recrystallization from methanol and with charcoal treatment gave pale yellow crystals (34.3 g.), m.p. 82°–84°.

B. Ethyl 4-Oxo-4H-pyrimido[2,1-a]isoquinoline-3-carboxylate

A stirred mixture of diethyl isoquinolylaminomethylenemalonate (32.0 g., 0.0986 mole) and diphenyl ether (125 ml.) under nitrogen was heated at a temperature of 235° for 15 minutes. The solid, m.p. 183°–184°, obtained upon cooling and dilution with Skellysolve B was recrystallized from ethanol to give salmon crystals (22 g., 83% yield), m.p. 189°–191°. An analytical sample, recrystallized from ethanol, had m.p. 190°–192°.

Anal. Calcd for $C_{15}H_{12}N_2O_3$: C, 67.15; H, 4.51; N, 10.44. Found: C, 66.87; H, 4.49; N, 10.68.

EXAMPLE 2

4-Oxo-4H-pyrimido[2,1-a]isoquinoline-3-carboxylic Acid (base hydrolysis of corresponding ester)

A mixture of ethyl 4-oxo-4H-pyrimido[2,1-a]isoquinoline-3-carboxylate (2.78 g., 0.010 mole), 1.0 N NaOH (15.0 ml.), $H_2O$ (40 ml.) and ethanol (30 ml.) was refluxed for 15 minutes. The mixture was filtered and the cooled filtrate acidified with 15.0 ml. of 1.0 N HCl to precipitate crude acid (2.36 g.), m.p. 193°-223°. Two recrystallizations from 2-methoxyethanol gave peach needles, m.p. 252°-253.5°.

Anal. Calcd for $C_{13}H_8N_2O_3$: C, 65.00; H, 3.36; N, 11.66. Found: C, 64.83; H, 3.38; N, 11.78.

EXAMPLE 3

4-Oxo-4H-pyrimido[2,1-a]isoquinoline-3-carboxylic Acid (alternative method via intermediate VI)

A. Ethyl 4-Imino-4H-pyrimido[2,1-a]isoquinoline-3-carboxylate

A mixture of 1-aminoisoquinoline (14.4 g., 0.10 mole) and ethyl ethoxymethylenecyanoacetate (16.9 g., 0.10 mole) was plunged into an oil bath at 105°-110° and kept there for 10 minutes under a nitrogen atmosphere. During this time the mixture melted, evolved ethanol and set solid. The solid was crystallized from toluene to give bright yellow crystals (18 g., 67% yield) of ethyl 4-imino-4H-pyrimido[2,1-a]isoquinoline-3-carboxylate, m.p. 197°-199°. Another recrystallization from toluene provided an analytical sample, m.p. 199°-201°.

Anal. Calcd for $C_{15}H_{13}N_3O_2$: C, 67.40; H, 4.90; N, 15.72. Found: C, 67.53; H, 4.79; N, 15.96.

B. 4-Oxo-4H-pyrimido[2,1-a]isoquinoline-3-carboxylic Acid

A solution of ethyl 4-imino-4H-pyrimido[2,1-a]isoquinoline-3-carboxylate (1.0 g.) in acetic acid (20 ml.) and 37% hydrochloric acid (20 ml.) was refluxed for 35 minutes. The solution was cooled and diluted with $H_2O$ to precipitate the crude acid (760 mg.), m.p. 219°-231° (prior softening). Recrystallized material (2-methoxyethanol) and a m.p. of 249°-252° and mixed melting point of 252°-255° with product from Example 2.

EXAMPLE 4

Ethyl 7-Methoxy-4-oxo-4H-pyrimido[2,1-a]isoquinoline-3-carboxylate (via intermediate IV)

A. Diethyl 4-Methoxyisoquinolylaminomethylenemalonate

A mixture of 1-amino-4-methoxyisoquinoline (297 mg., 1.7 mmoles) and diethyl ethoxymethylenemalonate (370 mg., 1.7 mmoles) was plunged into an oil bath at 110° and kept there for 6 minutes. The mixture melted and then solidified. The crude product, m.p. 150°-153°, was used without purification.

B. Ethyl 7-Methoxy-4-oxo-4H-pyrimido[2,1-a]isoquinoline-3-carboxylate

A mixture A mixture of diethyl 4-methoxyisoquinolylaminomethylenemalonate (460 mg., 1.33 mmoles) and diphenyl ether (4.6 ml.) was placed in an oil bath at 210°, the temperature of which, was increased to 260° during 5 minutes. Dilution of the solution with Skellysolve B caused the product (315 mgs., 79% yield), m.p. 190°-193°, to separate. Recrystallization from ethyl acetate raised the m.p. to 202°-204°.

EXAMPLE 5

7-Hydroxy-4-oxo-4H-pyrimido[2,1-a]isoquinoline-3-carboxylic Acid (acid hydrolysis of corresponding ester)

A suspension of ethyl 7-methoxy-4-oxo-4H-pyrimido[2,1-a]isoquinoline-3-carboxylate (240 mg., 0.83 mmole) in a mixture of acetic (4 ml.) and 37% hydrochloric (2 ml.) acids was refluxed for 2 hours. The mixture was flash evaporated to dryness, diluted with water and the precipitated solid collected and crystallized from acetic acid with charcoal treatment to give straw needles of the title acid, m.p. 273°-276°.

EXAMPLE 6

Ethyl 6,7-Dihydro-4-oxo-4H-pyrimido[2,1-a]isoquinoline-3-carboxylate (catalytic hydrogenation of corresponding unsaturated ester)

A mixture of ethyl 4-oxo-4H-pyrimido[2,1-a]isoquinoline-3-carboxylate (2.68 g., 0.010 mole) in acetic acid (200 ml.) containing 10% palladium on carbon (1.0 g.) was shaken with hydrogen at an initial pressure of about 4 kg. cm.$^{-2}$ until the theoretical pressure drop was reached (3.3 hours). The mixture was filtered and the filtrate flash evaporated to dryness to leave an oil, which upon dilution with toluene and reconcentration to dryness gave colorless crystalline material, m.p. 117°-125°. Two recrystallizations from ethanol raised the m.p. to 139°-141°. This material was combined with product of similar purity which separated from the first ethanolic mother liquor, and the lot recrystallized from cyclohexane to give the analytical sample, m.p. 138.5°-140°.

Anal. Calcd for $C_{15}H_{14}N_2O_3$: C, 66.65; H, 5.22; N, 10.37. Found: C, 66.32; H, 5.34; N, 10.48.

EXAMPLE 7

6,7-Dihydro-4-oxo-4H-pyrimido[2,1-a]isoquinoline-3-carboxylic Acid (base hydrolysis of corresponding ester)

A mixture of ethyl 6,7-dihydro-4-oxo-4H-pyrimido[2,1-a]isoquinoline-3-carboxylate (1.81 g., 6.7 mmoles), 1.0 N NaOH (25 ml.) and 95% ethanol was refluxed for 20 l minutes. The resulting solution was cooled and acidified with 1.0 HCl (26 ml.) to precipitate the acid, which was crystallized from 2-methoxyethanol to give colorless crystals: 1.02 g. (63% yield), m.p. 215°-217°. An additional recrystallization from 2-methoxyethanol gave material with m.p. 215.5°-217°.

Anal. Calcd for $C_{13}H_{10}N_2O_3$: C, 64.46; H, 4.16; N, 11.57. Found: C, 64.18; H, 4.22; N, 11.46.

EXAMPLE 8

3-(1H-Tetrazol-5-yl)-4H-pyrimido[2,1-a]isoquinol-4-one (via intermediate V)

A. Ethyl 2-Cyano-3-(isoquinolylamino)acrylate

A mixture of 1-aminoisoquinoline (14.4 g., 0.10 mole) and ethyl ethoxymethylenecyanoacetate (16.9 g., 0.10 mole) was plunged into an oil bath at 105°-110° and kept there for 10 minutes under a nitrogen atmosphere. During this time the mixture melted, evolved ethanol and set solid. The solid was crystallized from toluene to give bright yellow crystals (18 g., 67% yield) of ethyl 4-imino-4H-pyrimido[2,1-a]isoquinoline-3-carboxylate, m.p. 197°–199°. Another recrystallization from toluene provided an analytical sample, m.p. 199°–201°.

The first toluene mother liquor was concentrated to about 150 ml. by boiling, and then diluted with Skellysolve B (100 ml.). The mixture was filtered and the filtrate flashed to dryness to leave a yellow solid which was crystallized from methanol to afford 5.5 g. of ethyl 2-cyano-3-(isoquinolylamino)acrylate, m.p. 129°–133°. An additional 1.7 g. of this material (27% total yield), m.p. 129°–131°, was obtained by concentration of the methanol mother liquor. Chromatography of this latter crop on silicic acid (60 g.) with chloroform, followed by recrystallization from methanol, gave the analytical sample, m.p. 129°–130°.

Anal. Calcd for $C_{15}H_{13}N_3O_2$: C, 67.40; H, 4.90; N, 15.72. Found: C, 67.10; H, 5.01; N, 15.78.

B.

3-(1H-Tetrazol-5-yl)-4H-pyrimido[2,1-a]isoquinol-4-one

Aluminum chloride (2.98 g., 0.0224 mole) was cautiously added to stirred, cooled (ice-$H_2O$) tetrahydrofuran (150 ml.). Sodium azide (4.36 g., 0.0672 mole) was then added, and the resulting mixture refluxed for 0.5 hour to complete the formation of the aluminum azide.

Ethyl 2-cyano-3-(isoquinolylamino)acrylate (4.93 g., 0.0184 mole) was added to the cooled mixture. The resulting mixture was refluxed for 20 hours, flash evaporated to dryness, and diluted with water (200 ml.). The aqueous mixture was acidified with 37% hydrochloric acid (20 ml.). The solid, m.p. 260°–290° (decomp) was collected and stirred with 150 ml. of warm 2% $KHCO_3$-$H_2O$. The mixture was washed with diethyl ether, and the water insoluble material removed from the aqueous layer by filtration. Acidification of the filtrate with acetic acid precipitated the tetrazole, m.p. 304°–308° (decomp). Recrystallization from N,N-dimethylformamide gave buff needles: 1.1 g. (22.6% yield), m.p. 313°–314° (decomp).

Anal. Calcd for $C_{13}H_8N_6O$: C, 59.09; H, 3.05; N, 31.81. Found: C, 58.70; H, 3.02; N, 31.41.

EXAMPLE 9

Ethyl 6,7-Dihydro-9-methoxy-4-oxo-4H-pyrimido[2,1-a]isoquinoline-3-carboxylate (use of dialkyl ethoxymethylenemalonate procedure Diethyl ethoxymethylenemalonate (10.72 g., 0.0496 mole) was added to a stirred mixture at 25° of 1-amino-3,4-dihydro-6-methoxyisoquinoline (8.75 g., 0.0496 mole) in toluene (330 ml.). Stirring was continued for 10 minutes after which the temperature of the resulting yellow solution was raised to the reflux point during ten minutes. The solution was refluxed for 5 minutes and cooled to give ethyl 6,7-dihydro-9-methoxy-4-oxo-4H-pyrimido[2,1-a]isoquinoline-3-carboxylate, m.p. 158°–160° C. Successive recrystallizations from ethyl acetate and ethanol gave off-white flocculent needles: 10.3 g. (69% yield), m.p. 173°–175°.

Anal. Calcd for $C_{16}H_{16}N_2O_4$: C, 63.99; H, 5.37; N, 9.33. Found: C, 63.66; H, 5.36; N, 9.16.

EXAMPLE 10

Replacement of the 1-amino-3,4-dihydro-6-methoxyisoquinoline in the procedure of Example 9 with 1-amino-3,4-dihydro-7-methoxyisoquinoline, (±)-1-amino-4-ethyl-3,4-dihydroisoquinoline, 1-amino-3,4-dihydro-6,7-dimethoxyisoquinoline, and (±)-4-allyl-3,4-dihydro-7-methoxyisoquinoline, respectively, gave the following esters:

A. Ethyl 6,7-Dihydro-10-methoxy-4-oxo-4H-pyrimido[2,1-a]isoquinoline-3-carboxylate; (74% yield), m.p. 157.5°–158.5° from methanol (Anal. Calcd for $C_{16}H_{16}N_2O_4$: C, 63.99; H, 5.37; N, 9.33. Found: C, 63.38; H, 5.39; N, 9.18);

B. Ethyl (±)-7-Ethyl-6,7-dihydro-4-oxo-4H-pyrimido[2,1-a]isoquinoline-3-carboxylate; (27% yield), m.p. 98°–100° from methanol (Anal. Calcd for $C_{17}H_{18}N_2O_3$: C, 68.44; H, 6.08; N, 9.39. Found: C, 68.04; H, 5.80; N, 9.18);

C. Ethyl 6,7-Dihydro-9,10-dimethoxy-4-oxo-4H-pyrimido[2,1-a]isoquinoline-3-carboxylate; 45% yield after purification by chromatography on silica acid with chloroform, m.p. 208°–210° from ethanol (Anal. Calcd for $C_{17}H_{18}N_2O_5$: C, 61.81; H, 5.49; N, 8.48. Found: C, 61.68; H, 5.53; N, 8.48); and D. Ethyl (±)-7-Allyl-6,7-dihydro-10-methoxy-4-oxo-4H-pyrimido[2,1-a]-3-carboxylate; 24% yield after chromatography on silicic acid with $CHCl_3$ and crystallization from cyclohexane, m.p. 115°–115.5°

(Anal. Calcd for $C_{19}H_{20}N_2O_4$: C, 67.04; H, 5.92; N, 8.23. Found: C, 66.74; H, 5.74; N, 8.64)

EXAMPLE 11

The following 6,7-dihydro-4-oxo-4H-pyrimido-[2,1-a]isoquinoline-3-carboxylic acids were prepared by basic hydrolysis of the corresponding esters using the procedure described in Example 7:

A. 6,7-Dihydro-9-methoxy-4-oxo-4H-pyrimido[2,1-a]isoquinoline-3-carboxylic Acid (96% yield), m.p. 232.5°–234.5° from 2-methoxyethanol (Anal. Calcd for $C_{14}H_{12}N_2O_4$: C, 61.76; H, 4.44; N, 10.29. Found: C, 61.76; H, 4.75; N, 10.16);

B. 6,7-Dihydro-10-methoxy-4-oxo-4H-pyrimido[2,1-a]isoquinoline-3-carboxylic Acid (79% yield), m.p. 237°–239° from acetic acid-$H_2O$ (Anal. Calcd for $C_{14}H_{12}N_2O_4$: C, 61.76; H, 4.44; N, 10.29. Found: C, 61.41; H, 4.51; N, 10.13);

C. (±)-7-Ethyl-6,7-dihydro-4-oxo-4H-pyrimido[2,1-a]isoquinoline-3-carboxylic Acid (72% yield), m.p. 167°–169° from 95% ethanol (Anal. Calcd for $C_{15}H_{14}N_2O_3$: C, 66.65; H, 5.22; N, 10.37. Found: C, 66.28; H, 5.05; N, 10.03);

D. 6,7-Dihydro-9,10-dimethoxy-4-oxo-4H-pyrimido[2,1-a]isoquinoline-3-carboxylic Acid (91% yield), m.p. 264°–266° from 2-methoxyethanol (Anal. Calcd for $C_{15}H_{14}N_2O_5$: C, 59.60; H, 4.67; N, 9.27. Found: C, 59.51; H, 4.79; N, 9.01); and E. (±)-7-Allyl-6,7-dihydro-10-methoxy-4-oxo-4H-pyrimido[2,1-a]isoquinoline-3-carboxylic Acid (78% yield), m.p. 128°–130° from benzene-Skellysolve B (Anal. Calcd for $C_{17}H_{16}N_2O_4$: C, 65.37; H, 5.16; N, 8.97. Found: C, 65.10; H, 5.47; N, 8.70).

EXAMPLE 12

Ethyl 9-Methoxy-4-oxo-4H-pyrimido[2,1-a]isoquinoline-3-carboxylate (dehydrogenation of corresponding 6,7-dihydro ester)

A stirred mixture of ethyl 6,7-dihydro-9-methoxy-4-oxo-4H-pyrimido[2,1-a]isoquinoline-3-carboxylate (510 mgs.) in p-cymene (25 ml.) containing 10% palladium on carbon (150 mgs.) was refluxed for 7 hours. The mixture was flash evaporated to dryness and the residue extracted with boiling ethanol. The combined extracts were filtered and concentrated by boiling to give flocculent colorless needles of ethyl 9-methoxy-4-oxo-4H-pyrimido[2,1-a]isoquinoline-3-carboxylate: 420 mgs. (81% yield), m.p. 211.5°–212°. An additional recrystallization from ethanol raised the m.p. to 217°–218°.

Anal. Calcd for $C_{16}H_{14}N_2O_4$: C, 64.42; H, 4.73; N, 9.39. Found: C, 64.26; H, 4.65; N, 9.29.

EXAMPLE 13

Dehydrogenation of the appropriate 6,7-dihydro esters with palladium-on-carbon in boiling p-cymene according to the procedure of Example 12 gave the following products:

A. Ethyl 10-Methoxy-4-oxo-4H-pyrimido[2,1-a]isoquinoline-3-carboxylate (81% yield), m.p. 184°–186° from ethanol
(Anal. Calcd for $C_{16}H_{14}N_2O_4$: C, 64.42; H, 4.73; N, 9.39. Found: C, 64.04; H, 4.86; N, 9.52);

B. Ethyl 7-Ethyl-4-oxo-4H-pyrimido[2,1-a]isoquinoline-3-carboxylate (86% yield), m.p. 161°–163° from methanol
(Anal. Calcd for $C_{17}H_{16}N_2O_3$: C, 68.90; H, 5.44; N, 9.45. Found: C, 68.78; H, 5.29; N, 9.17); and C. Ethyl 9,10-Dimethoxy-4-oxo-4H-pyrimido[2,1-a]isoquinoline-3-carboxylate (70% yield), m.p. 264°–265° from acetic acid
(Anal. Calcd for $C_{17}H_{16}N_2O_5$: C, 62.19; H, 4.91; N, 8.53. Found: C, 61.72; H, 4.70; N, 8.40).

The latter ester was also prepared by oxidation with ceric ammonium nitrate (CAN), as follows: CAN (6.65 g., 12.12 mmoles) was added portionwise during fifteen minutes to a stirred solution of ethyl 6,7-dihydro-9,10-dimethoxy-4-oxo-4H-pyrimido[2,1-a]isoquinoline-3-carboxylate (1.0 g., 3.03 mmoles) in a mixture of acetic acid (25 ml.) and water (10 ml.) at about 35°. The solution was stirred at 25° for 1 hour and diluted with water. The precipitated solid was collected and washed with water, followed by acetone to give 400 mgs. (40% yield) of product, m.p. 264° and mixed m.p. of 263°–264° with material from the preceding experiment.

EXAMPLE 14

Ethyl 7-Allyl-10-methoxy-4-oxo-4H-pyrimido[2,1-a]isoquinoline-3-carboxylate (dehydrogenation of 6,7-dihydro ester)

A mixture of ethyl 7-allyl-6,7-dihydro-10-methoxy-4-oxo-4H-pyrimido[2,1-a]isoquinoline-3-carboxylate (1.5 g., 4.41 mmoles) and DDQ (1.1 g., 4.85 mmoles) in toluene (30 ml.) containing acetic acid (0.05 ml.) was refluxed for 18 hours. The mixture was filtered and the filtrate concentrated to dryness. Trituration of the residue with methanol gave a solid which was recrystallized from ethanol to give 201 mgs. of brown crystals, m.p. 182°–186°. The methanol mother liquor was concentrated to dryness and the residue chromatographed on silicic acid with toluene-acetone (20:1) to give additional product (230 mgs.), m.p. 177°–183° after recrystallization from ethanol. The material with m.p. 182°–186° was chromatographed in a similar manner and the product so obtained combined with the material with m.p. 177°–183° and the lot recrystallized from ethanol to give yellow needles of the title compound, m.p. 187°–188°.

Anal. Calcd for $C_{19}H_{18}N_2O_4$: C, 67.44; H, 5.63; N, 8.28. Found: C, 67.35; H, 5.52; N, 8.09.

EXAMPLE 15

Ethyl 10-Methoxy-4-oxo-7-propyl-4H-pyrimido[2,1-a]isoquinoline-3-carboxylate (dehydrogenation and reduction of allyl to propyl)

A mixture of ethyl (±)-7-allyl-6,7-dihydro-10-methoxy-4-oxo-4H-pyrimido[2,1-a]isoquinoline-3-carboxylate (190 mgs.) in p-cymene (5 ml.) containing 10% palladium on carbon (50 mgs.) was refluxed for 4 hours. The mixture was cooled, diluted with methylene chloride and filtered to remove the catalyst. The filtrate was evaporated to dryness in vacuo and the residue recrystallized from ethanol, with charcoal treatment, to give yellow needles of title product (119 mgs., 63%), m.p. 187°–188°.

Anal. Calcd for $C_{19}H_{20}N_2O_4$: C, 67.04; H, 5.92; N, 8.23. Found: C, 66.58; H, 5.68; N, 8.17.

EXAMPLE 16

10-Methoxy-4-oxo-4H-pyrimido[2,1-a]isoquinoline-3-carboxylic acid (hydrolysis of corresponding ester)

A solution of ethyl 10-methoxy-4-oxo-4H-pyrimido[2,1-a]isoquinoline-3-carboxylate (3.0 g., 0.010 mole) in a mixture of acetic acid (45 ml.) and 37% hydrochloric acid (23 ml.) was refluxed for 45 minutes. The mixture was cooled, diluted with water, and the yellow solid collected and dried to give the title acid: 2.6 g.(96% yield) m.p. 261°–263°. Recrystallization from acetic acid followed by n-butyl acetate gave the analytical sample, m.p. 262°–264°.

Anal. Calcd for $C_{14}H_{10}N_2O_4$: C, 62.22; H, 3.73; N, 10.37. Found: C, 62.15; H, 3.71; N, 10.29.

EXAMPLE 17

The following 4-oxo-4H-pyrimido[2,1-a]isoquinoline-3-carboxylic acids were prepared by hydrolysis of the corresponding ethyl esters according to the procedure of Example 16.

A. 7-Ethyl-4-oxo-4H-pyrimido[2,1-a]isoquinoline-3-carboxylic Acid (58% yield), m.p. 221°–223° from acetic acid-water
(Anal. Calcd for $C_{15}H_{12}N_2O_3$: C, 67.15; H, 4.51; N, 10.44. Found: C, 66.85; H, 4.54; N, 10.35);

B. 9,10-Dimethoxy-4-oxo-4H-pyrimido[2,1-a]isoquinoline-3-carboxylic Acid (89% yield), m.p. 298°–301° from 2-methoxyethanol
(Anal. Calcd for $C_{15}H_{12}N_2O_5$: C, 60.00; H, 4.03; N, 9.33. Found: C, 59.65; H, 4.23; N, 9.34);

C. 7-Allyl-10-methoxy-4-oxo-4H-pyrimido[2,1-a]isoquinoline-3-carboxylic Acid (39% yield), m.p. 207°–210° from acetic acid
(Anal. Calcd for $C_{17}H_{14}N_2O_4$: C, 65.80; H, 4.55; N, 9.03. Found: C, 65.50; H, 4.76; N, 9.08); and D. 10-Methoxy-4-oxo-7-propyl-4H-pyrimido[2,1-a]isoquinoline-3-carboxylic Acid, m.p. 245°–245.5° from acetic acid (Anal. Calcd for $C_{17}H_{16}N_2O_4$: C, 65.37; H, 5.16; N, 8.97. Found: C, 65.32; H, 5.40; N, 8.78).

EXAMPLE 18

9-Methoxy-4-oxo-4H-pyrimido[2,1-a]isoquinoline-3-carboxylic Acid (base hydrolysis of corresponding ester)

9-Methoxy-4-oxo-4H-pyrimido[2,1-a]isoquinoline-3-carboxylic acid, m.p. 302°–304° from N,N-dimethylformamide, was prepared in 59% yield from the ethyl ester by hydrolysis with base according to the procedure of Example 2.

Anal. Calcd for $C_{14}H_{10}N_2O_4$: C, 62.22; H, 3.73; N, 10.37. Found: C, 61.85; H, 3.95; N, 10.60.

EXAMPLE 19

6,7-Dihydro-10-hydroxy-4-oxo-4H-pyrimido[2,1-a]isoquinoline-3-carboxylic Acid (acid hydrolysis of corresponding ester)

A solution of ethyl 6,7-dihydro-10-methoxy-4-oxo-4H-pyrimido[2,1-a]isoquinoline-3-carboxylate (5.0 g., 0.0175 mole) in 48% hydrobromic acid (125 ml.) was refluxed for 4 hours. The solution was cooled and the yellow product collected, washed with water, and dissolved in warm 0.5 N NaOH (80 ml.). The basic solution was treated with decolorizing carbon, filtered and the filtrate acidified with hydrochloric acid. The precipitated material was washed on the filter successively with water, ethanol and acetone to give 3.5 g. (81% yield) of the title acid, m.p. 326°–327°.

Anal. Calcd for $C_{13}H_{10}N_2O_4$: C, 60.46; H, 3.90; N, 10.85. Found: C, 60.27; H, 3.73; N, 10.74.

EXAMPLE 20

6,7-Dihydro-9,10-dihydroxy-4-oxo-4H-pyrimido[2,1-a]isoquinoline-3-carboxylic Acid (acid hydrolysis of ester)

Ethyl 6,7-dihydro-9,10-dimethoxy-4-oxo-4H-pyrimido[2,1-a]isoquinoline-3-carboxylate was treated with 48% hydrogen bromide as described in Example 19 to give a 82% yield of the title acid, m.p. 308°–314°. Recrystallization from N,N-dimethylformamide gave the analytical sample, m.p. 321°–323°.

Anal. Calcd for $C_{13}H_{10}N_2O_5$: C, 56.93; H, 3.68; N, 10.22. Found: C, 56.42; H, 3.79; N, 10.24.

EXAMPLE 21

10-Isobutyryloxy-6,7-dihydro-4-oxo-4H-pyrimido[2,1-a]isoquinoline-3-carboxylic Acid (conversion of hydroxy substituent to isobutyryloxy)

Isobutyryl chloride (455 mg., 4.26 mmoles) was added to a stirred, cooled (ice-water) mixture of 6,7-dihydro-10-hydroxy-4-oxo-4H-pyrimido[2,1-a]isoquinoline-3-carboxylic acid (1.03 g., 3.87 mmoles) and triethylamine (785 mg., 7.75 mmoles) in methylene chloride (20 ml.). The mixture was concentrated to dryness and the residue was triturated with cold 1N HCl, and then crystallized from benzene to give the title compound 0.81 g. (64% yield). The product was recrystallized successively from ethyl acetate and methanol to give the analytical sample, m.p. 183°–185°.

Anal. Calcd for $C_{17}H_{16}N_2O_5$: C, 62.19; H, 4.91; N, 8.53. Found: C, 62.29; H, 4.94; N, 8.51.

EXAMPLE 22

Ethyl (±)-7-Formylmethyl-6,7-dihydro-10-methoxy-4-oxo-4H-pyrimido[2,1-a]isoquinoline-3-carboxylate and Ethyl (±)-6,7-Dihydro-7-(2,2-dimethoxyethyl)-10-methoxy-4-oxo-4H-pyrimido[2,1-a]isoquinoline-3-carboxylate (ozonolysis of allyl-substituted product and treatment with a (lower)alkanol)

A mixture of ozone in air was bubbled into a stirred solution at about −70° of ethyl (±)-7-allyl-6,7-dihydro-10-methoxy-4-oxo-4H-pyrimido[2,1-a]isoquinoline-3-carboxylate (950 mgs., 2.77 mmoles) in methylene chloride (25 ml.) until a pale blue color persisted. The excess ozone was removed with a stream of nitrogen. Dimethyl sulfide (1 ml.) was added and the solution stirred for one hour at ambient temperature and then concentrated to dryness. A solution of the residue in methanol (5 ml.) was allowed to stand at 25° for 4 days and then concentrated to dryness. Chromatography of the residue on silicic acid with toluene-acetone (10:1) gave the aldehyde (60 mgs.), m.p. 158°–160° from ethyl acetate and the corresponding acetal (350 mgs.), m.p. 112°–114° from cyclohexane. The acetal was recrystallized again from cyclohexane to give the analytical sample, m.p. 112°–113.5°.

Anal. Calcd for $C_{20}H_{24}N_2O_6$: C, 61.84; H, 6.23; N, 7.21. Found: C, 61.79; H, 6.40; N, 7.14.

In a repeat of the above experiment the aldehyde, m.p. 154.5°–157° from ethyl acetate, was isolated in 38% yield when the methanol was omitted from the workup.

EXAMPLE 23

(±)-7-Ethyl-6,7-dihydro-3-(1H-tetrazol-5-yl)-4H-pyrimido[2,1-a]isoquinol-4-one (via nitrile VII)

A.

(±)-7-Ethyl-6,7-dihydro-4-oxo-4H-pyrimido[2,1-a]isoquinoline-3-carboxamide

A mixture of (±)-7-ethyl 6,7-dihydro-4-oxo-4H-pyrimido[2,1-a]isoquinoline-3-carboxylate (1.0 g.) and liquid ammonia (25 ml.) in a steel bomb was heated on a steam bath for 1.5 hours. Removal of the ammonia left flocculent crystals of amide: 900 mgs. (100% yield), m.p. 197°–202°. Recrystallization from methanol gave colorless crystals, m.p. 205°–207°.

Anal. Calcd for $C_{15}H_{15}N_3O_2$: C, 66.90; H, 5.61; N, 15.61. Found: C, 66.37; H, 5.31; N, 15.42.

B.

(±)-7-Ethyl-6,7-dihydro-4-oxo-4H-pyrimido[2,1-a]isoquinoline-3-carbonitrile

A mixture of (±)-7-ethyl-6,7-dihydro-4-oxo-4H-pyrimido[2,1-a]isoquinoline-3-carboxamide (800 mg.) and phosphorus oxychloride (8 ml.) was refluxed for 2 hours. The mixture was flash evaporated to dryness and the residue partitioned between methylene chloride and aqueous potassium carbonate. The organic layer was dried over sodium sulfate and concentrated to dryness to leave 600 mgs. (80% yield) of nitrile, m.p. 145°–148°. Recrystallization from methanol gave chunky yellow crystals, m.p. 153°–154°.

Anal. Calcd for $C_{15}H_{13}N_3O$: C, 71.69; H, 5.21; N, 16.72. Found: C, 71.31; H, 5.11; N, 16.75.

C.
(±)-7-Ethyl-6,7-dihydro-3-(1H-tetrazol-5-yl)-4H-pyrimido[2,1-a]isoquinol-4-one A mixture of (±)-7-ethyl-6,7-dihydro-4-oxo-4H-pyrimido[2,1-a]isoquinoline-3-carbonitrile (208 mg., 0.836 mmole), sodium azide (59.8 mg., 0.92 mmole), and ammonium chloride (49.1 mg., 0.92 mmole) in N,N-dimethylformamide (2 ml.) was stirred for 19 hours at an oil bath temperature of 120°. The mixture was diluted with water and acidified with dilute hydrochloric acid to precipitate 215 mg. (87% yield) of the tetrazole, m.p. 254°–258° with decomposition. Recrystallization from acetic acid provided pale yellow crystals of the analytical sample, m.p. 282°–283.5° with decomposition.

Anal. Calcd for $C_{15}H_{14}N_6O$: C, 61.21; H, 4.79; N, 28.56. Found: C, 61.44; H, 4.81; N, 28.66.

EXAMPLE 24
6,7-Dihydro-9,10-dimethoxy-3-(1H-tetrazol-5-yl)-4H-pyrimido[2,1-a]isoquinol-4-one (via nitrile VII)

A.
6,7-Dihydro-9,10-dimethoxy-4-oxo-4H-pyrimido[2,1-a]isoquinoline-3-carboxamide In a manner similar to that described in Example 23A, ethyl 6,7-dihydro-9,10-dimethoxy-4-oxo-4H-pyrimido[2,1-a]isoquinoline-3-carboxylate was converted into the amide in 92% yield, m.p. 313°–315° from 2-methoxyethanol.

Anal. Calcd for $C_{15}H_{15}N_3O_4$: C, 59.79; H, 5.02; N, 13.95. Found: C, 59.62; H, 5.09; N, 13.94.

B.
6,7-Dihydro-9,10-dimethoxy-4-oxo-4H-pyrimido[2,1-a]isoquinoline-3-carbonitrile In a manner similar to that described in Example 23B, 6,7-dihydro-9,10-dimethoxy-4-oxo-4H-pyrimido[2,1-a]isoquinoline-3-carboxamide was dehydrated to the nitrile in 93% yield, m.p. 261°–262° from acetic acid.

Anal. Calcd for $C_{15}H_{13}N_3O_3$: C, 63.59; H, 4.63; N, 14.83. Found: C, 63.47; H, 4.82; N, 14.79.

C.
6,7-Dihydro-9,10-dimethoxy-3-(1H-tetrazol-5-yl)-4H-pyrimido[2,1-a]isoquinol-4-one In a manner similar to that described in Example 23C, 6,7-dihydro-9,10-dimethoxy-4-oxo-4H-pyrimido[2,1-a]isoquinoline-3-carbonitrile was converted to the corresponding tetrazole in 57% yield, m.p. 286°–288° (decomp) from acetic acid.

Anal. Calcd for $C_{15}H_{14}N_6O_3$: C, 55.21; H, 4.32; N, 25.76. Found: C, 54.89; H, 4.39; N, 25.64.

EXAMPLE 25
7-Ethyl-3-(1H-tetrazol-5-yl)-4H-pyrimido[2,1-a]isoquinol-4-one (via nitrile VII')

A.
7-Ethyl-4-oxo-4H-pyrimido[2,1-a]isoquinoline-3-carbonitrile

A stirred mixture of (±)-7-ethyl-6,7-dihydro-4-oxo-4H-pyrimido[2,1-a]isoquinoline-3-carbonitrile (3.5 g.) and 10% palladium on carbon (1.5 g.) in p-cymene (50 ml.) was refluxed for 18 hours. The mixture was diluted with methylene chloride and filtered to remove the catalyst. The solvents were removed on a rotary evaporator and the residue crystallized from ethanol to give 1.6 g. (46% yield) of the title compound, m.p. 208°–211°. Successive recrystallizations from toluene and ethanol provided the analytical sample, m.p. 218°–219°.

Anal. Calcd for $C_{15}H_{11}N_3O$: C, 72.27; H, 4.45; N, 16.86. Found: C, 72.00; H, 4.65; N, 16.56.

B.
7-Ethyl-3-(1H-tetrazol-5-yl)-4H-pyrimido[2,1-a]isoquinol-4-one

Aluminum chloride (595 mg., 4.46 mmoles) was added to stirred, ice-cold tetrahydrofuran (40 ml.). Sodium azide (870 mg., 13.4 mmoles) was then added and the mixture refluxed for 0.5 hour to complete the formation of the aluminum azide.

7-Ethyl-4-oxo-4H-pyrimido[2,1-a]isoquinoline-3-carbonitrile (1.0 g., 4.05 mmoles) was added and the mixture refluxed for 18 hours. The mixture was diluted with water and acidified with 37% hydrochloric acid to precipitate the tetrazole. The crude tetrazole was heated with 5% sodium carbonate-water. The aqueous mixture was washed with ethyl acetate and the aqueous layer warmed with decolorizing carbon and filtered. Acidification of the filtrate with acetic acid precipitated 1.0 g. (85% yield) of the product, m.p. 301°–303° (decomp). Pale yellow needles, m.p. 310.5°–312° with decomposition, were obtained upon crystallization from 2-methoxyethanol.

Anal. Calcd for $C_{15}H_{12}N_6O$: C, 61.63; H, 4.14; N, 28.76. Found: C, 60.99; H, 4.07; N, 28.24.

EXAMPLE 26

Following the general procedures of Examples 1, 3–4 and 12–15, the following pyrimido[2,1-a]isoquinoline-3-carboxylic acid esters may be prepared by use of the appropriate 1-aminoisoquinoline starting material or by dehydrogenation of the corresponding saturated ester.

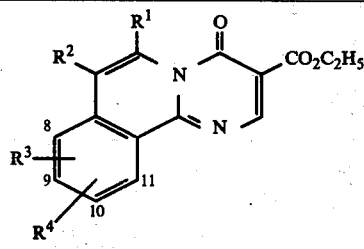

| $R^1$ | $R^2$ | $R^3$ | $R^4$ |
|---|---|---|---|
| $CH_3$ | H | H | H |
| H | $-OCH_2CH_3$ | H | H |

-continued

Structure: tricyclic compound with R¹ at top position, carbonyl O, N, CO₂C₂H₅ group; R² on ring; fused benzene ring with positions 8, 9, 10, 11 bearing R³ and R⁴.

| R¹ | R² | R³ | R⁴ |
|---|---|---|---|
| —C(CH₃)₃ | H | H | H |
| C₆H₅ | H | H | H |
| H | H | 10-OCH₃ | H |
| H | H | 9-CH₃ | H |
| H | —CH₂C₆H₅ | H | H |
| H | F | H | H |
| H | Cl | H | H |
| H | Br | H | H |
| H | I | H | H |
| H | —OCH₃ | H | H |
| H | —O—CH₂(CH₂)₂CH₃ | H | H |
| CH₃ | —OCH₃ | H | H |
| n-C₄H₉ | —OCH₂CH₃ | H | H |
| C₆H₅ | —OCH₃ | H | H |
| H | OH | H | H |
| H | —CH₂C₆H₅ | 9-OCH₃ | 10-OCH₃ |
| H | —CH₂C₆H₅ | 10-OCH₃ | 11-OCH₃ |
| H | —CH=CH₂ | H | H |
| H | H | 11-OCH₃ | H |
| H | H | 8-CH₃ | H |
| H | H | 10-CH₃ | H |
| H | H | 11-CH₃ | H |
| H | —CH₂(CH₂)₂CH₃ | H | H |
| H | C₆H₅ | H | H |
| H | H | 9-Br | H |
| H | H | 9-Cl | 10-Cl |
| H | H | 9,10-methylenedioxy | |
| H | H | 10-Cl | H |
| H | H | 10-Br | H |
| H | CH₃ | 10-Cl | H |
| H | H | 10-OH | 11-OH |
| H | H | 8-OCH₃ | H |
| H | CH₃ | 9-OCH₃ | 11-OCH₃ |
| H | H | 10,11-methylenedioxy | |
| H | H | 10-C₂H₅ | H |
| H | H | 10-CH(CH₃)₂ | H |
| H | H | 10-C(CH₃)₃ | H |
| H | —CH₂CH=CH₂ | H | H |
| H | —C≡CH | H | H |
| H | —CH₂C≡CH | H | H |
| H | C₆H₅COO— | H | H |
| H | CH₃COO— | H | H |
| H | —C₂H₅COO—H | H | H |
| H | —C(CH₃)₃ | H | H |
| H | —CH₂CH(CH₃)₂ | H | H |
| H | —CH(CH₃)CH₂CH₃ | H | H |
| H | —CH(CH₃)₂ | H | H |
| H | —CH₂CH₂CH₃ | H | H |
| H | —CH₂CHO | H | 10-OCH₃ |
| H | —CH₂CH(OCH₃)₂ | H | 10-OCH₃ |
| H | —CH₂CH(OC₂H₅)₂ | H | 10-OCH₃ |
| H | —CH₂CH₂OH | H | 10-OCH₃ |
| H | —CH₂CH(OH)CH₂OH | H | 10-OCH₃ |
| H | cyclopropyl-CH₂— | H | H |
| H | cyclobutyl-CH₂— | H | H |
| H | cyclohexyl- | H | H |
| H | cyclohexyl-CH₂CH₂— | H | H |
| H | H | 9-CF₃ | H |
| H | H | 9-CH₂CH=CH₂ | H |
| H | H | 9-n-C₃H₇ | H |
| H | H | 9-OC₂H₅ | H |
| H | H | 10-OH | H |
| H | H | 10-OCOCH(CH₂)₂ | H |

-continued

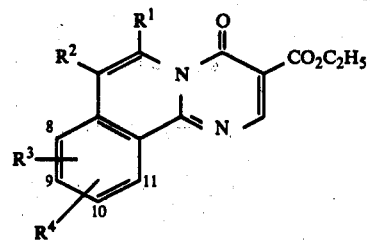

| R¹ | R² | R³ | R⁴ |
|---|---|---|---|
| H | H | 10-OCOC₆H₅ | H |
| H | H | 10-OCOCH₃ | H |
| H | H | 9-OH | 10-OH |
| H | H | 9-OCOCH₃ | 10-OCOCH₃ |

The esters prepared above may be subjected to acid or base hydrolysis to provide the corresponding 3-carboxylic acid compounds.

EXAMPLE 27

Following the general procedures of Examples 6, 9–10 and 21–22, the following 6,7-dihydropyrimido[2,1-a]isoquinoline esters may be prepared by use of the appropriate 1-amino-3,4-dihydroisoquinoline starting material or by catalytic hydrogenation of the corresponding pyrimido[2,1-a]isoquinoline-3-carboxylic acid ester.

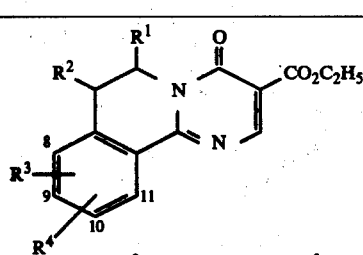

| R¹ | R² | R³ | R⁴ |
|---|---|---|---|
| CH₃ | H | H | H |
| H | n-C₄H₉ | H | H |
| H | C₆H₅ | H | H |
| H | H | 9-Br | H |
| H | H | 9-Cl | 10-Cl |
| H | H | 9,10-methylenedioxy | |
| H | H | 10-Cl | H |
| H | H | 10-Br | H |
| H | CH₃ | 10-Cl | H |
| H | CH₃ | H | H |
| H | H | 8-OCH₃ | H |
| H | CH₃ | H | H |
| H | H | 8-CH₃ | H |
| H | H | 9-CH₃ | H |
| H | H | 10-CH₃ | H |
| H | H | 10-C₂H₅ | H |
| H | H | 10-(CH₃)₂CH | H |
| H | H | 10-(CH₃)₃C | H |
| H | H | 9-OCH₃ | 11-OCH₃ |
| H | H | 10,11-methylenedioxy | |
| C₂H₅ | H | H | H |
| H | H | 9-OH | H |
| H | H | 9-C₆H₅COO | H |
| H | H | 9-CH₃COO | H |
| H | H | 9-C₂H₅COO | H |
| H | H | 9-OH | 11-OH |
| H | —CH₂CH(OC₂H₅)₂ | 10-OCH₃ | H |
| C₆H₅ | H | H | H |
| H | CH₂=CHCH₂— | H | H |
| H | —C≡CH | H | H |
| H | —CH₂C≡CH | H | H |
| H | —CH₂CH₂CH₃ | H | H |
| H | —CH(CH₃)₂ | H | H |
| H | —CH(CH₃)CH₂CH₃ | H | H |
| H | —CH₂CH(CH₃)₂ | H | H |
| H | —C(CH₃)₃ | H | H |
| H | —CH₂CH(OH)CH₂OH | H | 10-OCH₃ |
| H | —CH₂CH₂OH | H | 10-OCH₃ |

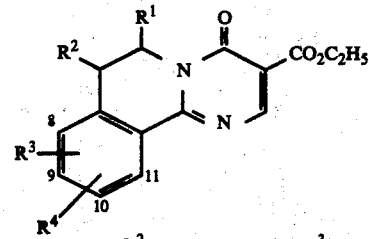

| R¹ | R² | R³ | R⁴ |
|---|---|---|---|
| H | ▱—CH₂CH₂— | H | H |
| H | cyclohexyl | H | H |
| H | cyclohexyl-CH₂— | H | H |
| H | H | 9-CF₃ | H |
| n-C₄H₉ | —OCH₂CH₃ | H | H |
| —C(CH₃)₃ | H | H | H |
| H | —CH₂C₆H₅ | H | H |
| C₆H₅ | —OCH₃ | H | H |
| H | OH | H | H |
| H | C₆H₅COO— | H | H |
| H | CH₃COO— | H | H |
| H | H | 9-CH₂CH=CH₂ | H |
| H | H | H | H |

The esters prepared above may be subjected to acidic or basic hydrolysis to provide the corresponding 3-carboxylic acid compounds.

EXAMPLE 28

Following the general procedures of Examples 8 and 25, the following tetrazole compounds may be prepared by use of the appropriate 1-aminoisoquinoline or 1-3,4-dihydroisoquinoline starting material.

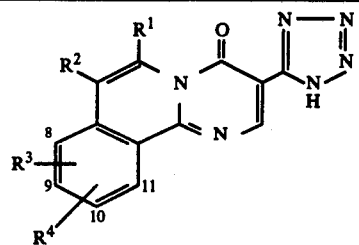

| $R^1$ | $R^2$ | $R^3$ | $R^4$ |
|---|---|---|---|
| $CH_3$ | H | H | H |
| H | $-OCH_2CH_3$ | H | H |
| $C(CH_3)_3$ | H | H | H |
| $C_6H_5$ | H | H | H |
| H | H | 10-$OCH_3$ | H |
| H | H | 9-$CH_3$ | H |
| H | $-CH_2C_6H_5$ | H | H |
| H | F | H | H |
| H | Cl | H | H |
| H | Br | H | H |
| H | I | H | H |
| H | $-OCH_3$ | H | H |
| $CH_3$ | $-O-CH_2(CH_2)_2CH_3$ | H | H |
| n-$C_4H_9$ | $-OCH_3$ | H | H |
| $C_6H_5$ | $-OCH_2CH_3$ | H | H |
| H | $-OCH_3$ | H | H |
| H | OH | H | H |
| H | $-CH_2C_6H_5$ | 9-$OCH_3$ | 10-$OCH_3$ |
| H | $-CH_2C_6H_5$ | 10-$OCH_3$ | 11-$OCH_3$ |
| H | $-CH=CH_2$ | H | H |
| H | $-CH_2CH=CH_2$ | H | H |
| H | H | 10-$OCH_3$ | H |
| H | H | 11-$OCH_3$ | H |
| H | H | 8-$CH_3$ | H |
| H | H | 10-$CH_3$ | H |
| H | H | 11-$CH_3$ | H |
| H | $-CH_2(CH_2)_2CH_3$ | H | H |
| H | $C_6H_5$ | H | H |
| H | H | 9-Br | H |
| H | H | 9-Cl | 10-Cl |
| H | H | 9,10-methylenedioxy | |
| H | H | 10-Cl | H |
| H | H | 10-Br | H |
| H | $CH_3$ | 10-Cl | H |
| H | H | 10-OH | 11-OH |
| H | H | 8-$OCH_3$ | H |
| H | $CH_3$ | H | H |
| H | H | 9-$OCH_3$ | 11-$OCH_3$ |
| H | H | 10,11-methylenedioxy | |
| H | H | 10-$C_2H_5$ | H |
| H | H | 10-$CH(CH_3)_2$ | H |
| H | H | 10-$C(CH_3)_3$ | H |
| H | $-CH_2CH=CH_2$ | H | H |
| H | $-C\equiv CH$ | H | H |
| H | $-CH_2C\equiv CH$ | H | H |
| H | $C_6H_5COO-$ | H | H |
| H | $CH_3COO-$ | H | H |
| H | $C_2H_5COO-$ | H | H |
| H | $-CH(H_3)_2$ | H | H |
| H | $-CH_2CH_2CH_3$ | H | H |
| H | $-CH(CH_3)CH_2CH_3$ | H | H |
| H | $-CH_2CH(CH_3)_2$ | H | H |
| H | $-C(CH_3)_3$ | H | H |
| H | $-CH_2CHO$ | H | H |
| H | $-CH_2CH(OCH_3)_2$ | 10-$OCH_3$ | H |
| H | $-CH_2CH(OC_2H_5)_2$ | 10-$OCH_3$ | H |
| H | $-CH_2CH_2OH$ | 10-$OCH_3$ | H |
| H | $-CH_2CH(OH)CH_2OH$ | 10-$OCH_3$ | H |
| H | ▷—$CH_2-$ | H | H |
| H | □—$CH_2-$ | H | H |
| H | ⬡ (cyclohexyl) | H | H |
| H | ⬡—$CH_2-$ (cyclohexylmethyl) | H | H |
| H | ⬡—$CH_2CH_2-$ | H | H |
| H | H | 9-$CF_3$ | H |
| H | H | 9-$CH_2CH=CH_2$ | H |
| H | H | 9-n-$C_3H_7$ | H |

-continued

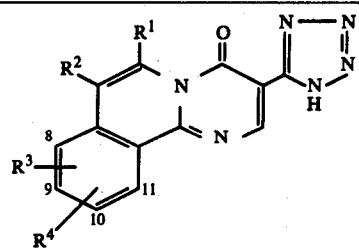

| $R^1$ | $R^2$ | $R^3$ | $R^4$ |
|---|---|---|---|
| H | H | 9-$OC_2H_5$ | H |
| H | H | 10-OH | H |
| H | H | 10-$OCOCH(CH_3)_2$ | H |
| H | H | 10-$OCOC_6H_5$ | H |
| H | H | 10-$OCOCH_3$ | H |
| H | H | 9-OH | 10-OH |
| H | H | 9-$OCOCH_3$ | 10-$OCOCH_3$ |

EXAMPLE 29

Following the general procedures of Examples 23–24, the following tetrazole compounds may be prepared by use of the appropriate 1-amino-3,4-dihydroisoquinoline or 1-aminoisoquinoline starting material.

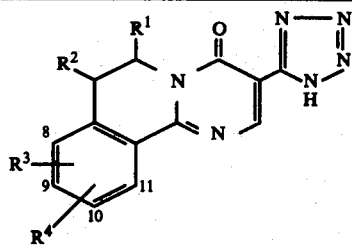

| $R^1$ | $R^2$ | $R^3$ | $R^4$ |
|---|---|---|---|
| $CH_3$ | H | H | H |
| H | n-$C_4H_9$ | H | H |
| H | $C_6H_5$ | H | H |
| H | H | 9-Br | H |
| H | H | 9-Cl | 10-Cl |
| H | H | 9,10-methylenedioxy | |
| H | H | 10-Cl | H |
| H | H | 10-Br | H |
| H | $CH_3$ | 10-Cl | H |
| H | $CH_3$ | H | H |
| H | H | 8-$OCH_3$ | H |
| H | $CH_3$ | H | H |
| H | H | 8-$CH_3$ | H |
| H | H | 9-$CH_3$ | H |
| H | H | 10-$CH_3$ | H |
| H | H | 10-$C_2H_5$ | H |
| H | H | 10-$(CH_3)_2CH$ | H |
| H | H | 10-$(CH_3)_3C$ | H |
| H | H | 9-$OCH_3$ | 11-$OCH_3$ |
| H | H | 10,11-methylenedioxy | |
| $C_2H_5$ | H | H | H |
| H | H | 9-OH | H |
| H | H | 9-$C_6H_5COO$ | H |
| H | H | 9-$CH_3COO$ | H |
| H | H | 9-$C_2H_5COO$ | H |
| H | H | 9-OH | 11-OH |
| H | $-CH_2CH(OC_2H_5)_2$ | 10-$OCH_3$ | H |
| H | $-CH_2CH(OCH_3)_2$ | 10-$OCH_3$ | H |
| H | $-CH_2CHO$ | 10-$OCH_3$ | H |
| $C_6H_5$ | H | H | H |
| H | $CH_2=CHCH_2-$ | H | H |
| H | $-C\equiv CH$ | H | H |
| H | $-CH_2C\equiv CH$ | H | H |
| H | $-CH_2CH(OH)CH_2OH$ | 10-$OCH_3$ | H |
| H | $-CH_2CH_2OH$ | 10-$OCH_3$ | H |
| H | ▷—$CH_2CH-$ | H | H |

-continued

| R¹ | R² | R³ | R⁴ |
|---|---|---|---|
| H | cyclohexyl | H | H |
| H | cyclohexyl-CH₂— | H | H |
| H | —CH₂CH₂CH₃ | H | H |
| H | —CH(CH₃)₂ | H | H |
| H | —CH(CH₃)CH₂CH₃ | H | H |
| H | —CH₂CH(CH₃)₂ | H | H |
| H | —C(CH₃)₃ | H | H |
| H | H | 9-CF₃ | H |
| n-C₄H₉ | —OCH₂CH₃ | H | H |
| —C(CH₃)₃ | H | H | H |
| H | —CH₂C₆H₅ | H | H |
| C₆H₅ | —OCH₃ | H | H |
| H | OH | H | H |
| H | C₆H₅COO— | H | H |
| H | CH₃COO— | H | H |
| H | H | 9-CH₂CH=CH₂ | H |

EXAMPLE 30

Salt Formation

The carboxylic acid and tetrazole products of Examples 2-3, 5, 7-8, 11, 16-21 and 23-29 are converted to the corresponding sodium, potassium, ammonium, calcium, magnesium, barium, aluminum, triethylamine, n-propylamine, tri-n-butylamine, piperidine, ethanolamine, diethanolamine, triethanolamine, diethylaminoethylamine, ethylenediamine, pyrrolidine, benzylamine, tris(hydroxymethyl)aminomethane and N,N'-dibenzylethylenediamine salts by reaction with an equivalent of the appropriate metal hydroxide, ammonium hydroxide or amine in water or ethanol followed by filtration of the salt if it is insoluble or by evaporation of the solvent if the salt is soluble therein.

EXAMPLE 31

Ester Formation

A. (Lower)alkyl Esters:

The carboxylic acid products of Examples 2-3, 5, 7, 11, 16-21 and 26-27 may be converted to the corresponding methyl esters by mixing the appropriate acid in methanol and slowly adding with stirring a catalytic amount of concentrated sulfuric acid. The mixture is heated under reflux for several hours and the excess methanol then removed to give the desired methyl ester. Replacement of the methanol in the above procedure by other appropriate alcohols such as ethanol, propanol, isopropanol, butanol, isobutanol, etc. gives other (lower)alkyl ester derivatives of the indicated acids.

B. Di(lower)alkylamino(lower)alkyl Esters:

Di(lower)alkylamino(lower)alkyl esters may be prepared as follows:

The acid products of Examples 2-3, 5, 7, 11, 16-21 and 26-27 are converted to the corresponding acid chlorides in a manner similar to that described below for preparation of 4-oxo-4H-pyrimido[2,1-a]isoquinoline-3-carbonyl chloride:

4-Oxo-4H-pyrimido[2,1-a]isoquinoline-3-carbonyl chloride

Hydrochloric acid was bubbled into a stirred suspension of 4-oxo-4H-pyrimido[2,1-a]isoquinoline-3-carboxylic acid (1.2 g., 0.005 mole) in methylene chloride (100 ml.) for 3 minutes. Phosphorous pentachloride (2.60 g., 0.0125 mole) was added to the milky suspension and stirring continued for 18 hours at 25°. The insoluble acid chloride was collected, washed with methylene chloride, dried and used immediately.

The appropriate acid chloride is mixed with an equivalent amount of 3-dimethylamino-1-propanol in an inert organic solvent such as methylene chloride, N,N-dimethylformamide or pyridine and the mixture stirred at 25° for 18 hours if methylene chloride was employed or about 2 hours at about 70°-90° if N,N-dimethylformamide or pyridine were used. Removal of the solvent leaves the hydrochloride salt of the 3-dimethylamino-1-propyl ester. If desired the hydrochloride salt may be converted to the free base by treatment with cool aqueous sodium hydroxide. The ester or hydrochloride salt is purified by crystallization.

Similarly other di(lower)alkylamino(lower)alkanols such as 2-dimethylaminoethanol, 3-diethylamino-1-propanol or 2-diisopropylaminoethanol may be substituted for the 3-dimethylamino-1-propanol in the above experiment to give the corresponding esters.

C. 1-Glyceryl Esters:

Treatment of a mixture of an appropriate pyrimido[2,1-a]isoquinoline-3-carbonyl chloride in pyridine at about 0°-75° with an equimolar amount of 2,2-dimethyl-1,3-dioxolane-4-methanol (acetone ketal of glycerin) for about 2 hours gives the protected 1-glyceryl ester. Removal of the pyridine and treatment of the residue with dilute aqueous hydrochloric acid cleaves the ketal to give the desired ester, which is purified by crystallization.

D. Pivaloyloxymethyl Esters

The acid products of Examples 2-3, 5, 7, 11, 16-21, and 26-27 may be converted to the corresponding pivaloyloxymethyl esters by first mixing the appropriate acid with at least an equivalent amount of a base such as triethylamine in an inert organic solvent such as N,N-dimethylformamide of N,N-dimethylacetamide and then treating the stirred mixture with an equivalent amount of pivaloyloxymethyl chloride. The mixture is stirred at about 25° for 18 hours. Dilution of the mixture with water causes the pivaloyloxymethyl ester to separate, which is purified by crystallization.

Replacement of the pivaloyloxymethyl chloride with acetoxymethyl chloride, methoxymethyl chloride or 1-bromophthalide in the above examples produces the corresponding acetoxymethyl, methoxymethyl or phthalidyl esters, respectively.

We claim:

1. A compound of the formula

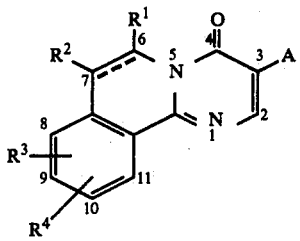

wherein A is tetrazol-5-yl or —CO₂R⁵ in which R⁵ is hydrogen or the residue of an easily cleavable ester group selected from the group consisting of (lower)alkyl, pivaloyloxymethyl, acetoxymethyl, methoxymethyl, phthalidyl, 1-glyceryl and di(lower)alkylamino(lower)alkyl, R¹ is hydrogen, (lower)alkyl or phenyl, R² is hydrogen, (lower)alkyl, (lower)alkenyl, (lower)alkynyl, hydroxy, (lower)alkoxy, R⁶—COO— in which R⁶ is (lower(alkyl or phenyl, di(lower)alkoxyethyl, formylmethyl, —CH₂CH(OH)CH₂OH, hydroxyethyl, phenyl, benzyl, C₃-C₆ cycloalkyl-C₁-C₂ alkyl, C₅-C₆ cycloalkyl or halogen and R³ and R⁴ are each independently hydrogen, (lower)alkyl, hydroxy, (lower)alkoxy, R⁶—COO— in which R⁶ is (lower)alkyl or phenyl, halogen, (lower)alkenyl or trifluoromethyl, or R³ and R⁴ taken together are methylenedioxy, and the dashed line represents an optional double bond, with the privisos that (1) R² may be halogen only where there is a double bond in the 6,7-position, (2) R³ and R⁴ taken together may not be adjacent t-butyl and (3) when either of R³ or R⁴ is trifluoromethyl, the other must be hydrogen; or a pharmaceutically acceptable cationic salt thereof when A is tetrazol-5-yl or —CO₂H.

2. A compound of claim 1 wherein A is tetrazol-5-yl.

3. A compound of claim 1 wherein A is —CO₂R⁵ in which R⁵ is hydrogen or the residue of an easily cleavable ester group selected from the group consisting of (lower)alkyl, pivaloyloxymethyl, acetoxymethyl, methoxymethyl, phthalidyl, 1-glyceryl and di(lower)alkylamino(lower)alkyl.

4. A compound of claim 1 wherein R¹ is hydrogen and R² is hydrogen, (lower)alkyl, (lower)alkenyl, hydroxy, (lower)alkoxy, R⁶—COO— in which R⁶ is (lower)alkyl or phenyl, di(lower)alkoxyethyl, formylmethyl, phenyl, benzyl, C₅-C₆ cycloalkyl or C₃-C₆ cycloalkyl-C₁-C₂ alkyl.

5. A compound of the formula

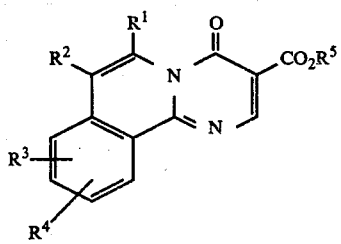

wherein R¹ is hydrogen, (lower)alkyl or phenyl, R² is hydrogen, (lower)alkyl, (lower)alkenyl, (lower)alkynyl, hydroxy, (lower)alkoxy, R⁶—COO— in which R⁶ is (lower)alkyl or phenyl, di(lower)alkoxyethyl, formylmethyl, —CH₂CH(OH)CH₂OH, hydroxyethyl, phenyl, benzyl, C₃-C₆ cycloalkyl-C₁-C₂ alkyl, C₅-C₆ cycloalkyl or halogen, R³ and R⁴ are each independently hydrogen, (lower)alkyl, hydroxy, (lower)alkoxy, R⁶—COO— in which R⁶ is (lower)alkyl or phenyl, halogen, (lower)alkenyl or trifluoromethyl, or R³ and R⁴ taken together are methylenedioxy, and R⁵ is hydrogen, pivaloyloxymethyl, acetoxymethyl, methoxymethyl, phthalidyl, 1-glyceryl or di(lower)alkylamino(lower)alkyl, with the provisos that (1) R³ and R⁴ taken together may not be adjacent t-butyl and (2) when either of R³ or R⁴ is trifluoromethyl, the other must be hydrogen; or a pharmaceutically acceptable cationic salt thereof when R⁵ is hydrogen.

6. A compound of claim 5 wherein R⁵ is hydrogen.

7. A compound of claim 5 wherein R⁵ is (lower)alkyl.

8. A compound of claim 5 wherein R⁵ is pivaloyloxymethyl, acetoxymethyl, methoxymethyl, phthalidyl, 1-glyceryl or di(lower)alkylamino(lower)alkyl.

9. A compound of claim 5 wherein R¹ is hydrogen and R² is hydrogen, (lower)alkyl, (lower)alkenyl, hydroxy, (lower)alkoxy, R⁶—COO— in which R⁶ is (lower)alkyl or phenyl, di(lower)alkoxyethyl, formylmethyl, phenyl, benzyl, C₅-C₆ cycloalkyl or C₃-C₆ cycloalkyl-C₁-C₂ alkyl.

10. A compound of the formula

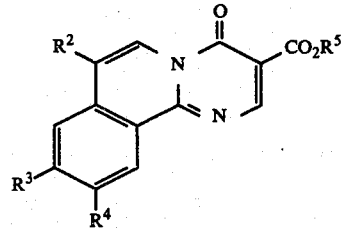

wherein R² is hydrogen, (lower)alkyl, (lower)alkenyl, hydroxy, (lower)alkoxy, R⁶—COO— in which R⁶ is (lower)alkyl or phenyl, di(lower)alkoxyethyl, formylmethyl, phenyl, benzyl, C₃-C₆ cycloalkyl-C₁-C₂ alkyl or C₅-C₆ cycloalkyl, R³ and R⁴ are each independently hydrogen, (lower)alkyl, hydroxy, (lower)alkoxy, R⁶—COO— in which R⁶ is (lower)alkyl or phenyl, halogen, (lower)alkenyl or trifluoromethyl or R³ and R⁴ taken together are methylenedioxy, R⁵ is hydrogen or (lower)alkyl, with the provisos that (1) R³ and R⁴ taken together may not be adjacent t-butyl and (2) when either of R³ or R⁴ is trifluoromethyl, the other must be hydrogen; or a pharmaceutically acceptable cationic salt thereof when R⁵ is hydrogen.

11. A compound of the formula

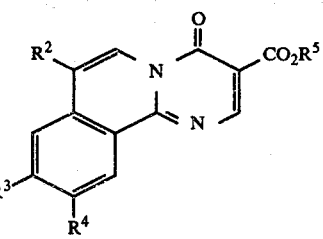

wherein R² is hydrogen, ethyl, hydroxy, allyl or n-propyl, R³ and R⁴ are each independently hydrogen or methoxy and R⁵ is hydrogen or ethyl; or a pharmaceutically acceptable cationic salt thereof when R⁵ is hydrogen.

12. The compound of claim 11 wherein R², R³ and R⁴ are hydrogen and R⁵ is ethyl.

13. The compound of claim 11 wherein R², R³, R⁴ and R⁵ are hydrogen.

14. The compound of claim 11 wherein $R^2$ and $R^4$ are hydrogen, $R^3$ is methoxy and $R^5$ is ethyl.

15. The compound of claim 11 wherein $R^2$, $R^4$ and $R^5$ are hydrogen and $R^3$ is methoxy.

16. The compound of claim 11 wherein $R^2$ and $R^3$ are hydrogen, $R^4$ is methoxy and $R^5$ is ethyl.

17. The compound of claim 11 wherein $R^2$, $R^3$ and $R^5$ are hydrogen and $R^4$ is methoxy.

18. The compound of claim 11 wherein $R^2$ and $R^5$ are ethyl and $R^3$ and $R^4$ are hydrogen.

19. The compound of claim 11 wherein $R^2$ is ethyl and $R^3$, $R^4$ and $R^5$ are hydrogen.

20. The compound of claim 11 wherein $R^2$ is hydroxy and $R^3$, $R^4$ and $R^5$ are hydrogen.

21. The compound of claim 11 wherein $R^2$ is hydrogen, $R^3$ and $R^4$ are methoxy and $R^5$ is ethyl.

22. The compound of claim 11 wherein $R^2$ and $R^5$ are hydrogen and $R^3$ and $R^4$ are methoxy.

23. The compound of claim 11 wherein $R^2$ is allyl, $R^3$ is hydrogen, $R^4$ is methoxy and $R^5$ is ethyl.

24. The compound of claim 11 wherein $R^2$ is allyl, $R^3$ and $R^5$ are hydrogen and $R^4$ is methoxy.

25. The compound of claim 11 wherein $R^2$ is n-propyl, $R^3$ is hydrogen, $R^4$ is methoxy and $R^5$ is ethyl.

26. The compound of claim 11 wherein $R^2$ is n-propyl, $R^3$ and $R^5$ are hydrogen and $R^4$ is methoxy.

27. A compound of the formula wherein $R^1$ is hydrogen, (lower)alkyl or phenyl, $R^2$ is hydrogen, (lower)alkyl, (lower)alkenyl, (lower)alkynyl, hydroxy, (lower)alkoxy, $R^6$—COO— in which $R^6$ is (lower)alkyl or phenyl, di(lower)alkoxyethyl, formylmethyl, —CH$_2$CH(OH)CH$_2$OH, hydroxyethyl, phenyl, benzyl, $C_3$-$C_6$ cycloalkyl-$C_1$-$C_2$ alkyl, or $C_5$-$C_6$ cycloalkyl, $R^3$ and $R^4$ are each independently hydrogen, (lower)alkyl, hydroxy, (lower)alkoxy, $R^6$—COO— in which $R^6$ is (lower)alkyl or phenyl, halogen, (lower)alkenyl or trifluoromethyl, or $R^3$ and $R^4$ taken together are methylenedioxy, and $R^5$ is hydrogen, pivaloyloxymethy, acetoxymethyl, methoxymethyl, phthalidyl, 1-glyceryl or di(lower)alkylamino(lower)alkyl, with the provisos that (1) $R^3$ and $R^4$ taken together may not be adjacent t-butyl and (2) when either of $R^3$ or $R^4$ is trifluoromethyl, the other must be hydrogen; or a pharmaceutically acceptable cationic salt thereof when $R^5$ is hydrogen.

28. A compound of claim 27 wherein $R^5$ is hydrogen.

29. A compound of claim 27 wherein $R^5$ is (lower)alkyl.

30. A compound of claim 27 wherein $R^5$ is pivaloyloxymethyl, acetoxymethyl, methoxymethyl, phthalidyl, 1-glyceryl or di(lower)alkylamino(lower)alkyl.

31. A compound of claim 27 wherein $R^1$ is hydrogen and $R^2$ is hydrogen, (lower)alkyl, (lower)alkenyl, hydroxy, (lower)alkoxy, $R^6$—COO— in which $R^6$ is (lower)alkyl or phenyl, di(lower)alkoxyethyl, formylmethyl, phenyl, benzyl, $C_5$-$C_6$ cycloalkyl or $C_3$-$C_6$ cycloalkyl-$C_1$-$C_2$ alkyl.

32. A compound of the formula wherein $R^2$ is hydrogen, (lower)alkyl, (lower)alkenyl, hydroxy, (lower)alkoxy, $R^6$—COO— in which $R^6$ is (lower)alkyl or phenyl, di(lower)alkoxyethyl, formylmethyl, phenyl, benzyl, $C_3$-$C_6$ cycloalkyl-$C_1$-$C_2$ alkyl or $C_5$-$C_6$ cycloalkyl, $R^3$ and $R^4$ are each independently hydrogen, (lower)alkyl, hydroxy, (lower)alkoxy, $R^6$—COO— in which $R^6$ is (lower)alkyl or phenyl, halogen, (lower)alkenyl or trifluoromethyl, or $R^3$ and $R^4$ taken together are methylenedioxy, and $R^5$ is hydrogen or (lower)alkyl, with the provisos that (1) $R^3$ and $R^4$ taken together may not be adjacent t-butyl and (2) when either of $R^3$ or $R^4$ is trifluoromethyl, the other must be hydrogen; or a pharmaceutically acceptable cationic salt thereof when $R^5$ is hydrogen.

33. A compound of the formula wherein $R^2$ is hydrogen, ethyl, allyl, formylmethyl or dimethoxyethyl, $R^3$ and $R^4$ are each independently hydrogen, methoxy, hydroxy or isobutyryloxy and $R^5$ is hydrogen or ethyl; or a pharmaceutically acceptable cationic salt thereof when $R^5$ is hydrogen.

34. The compound of claim 33 wherein $R^2$, $R^3$ and $R^4$ are hydrogen and $R^5$ is ethyl.

35. The compound of claim 33 wherein $R^2$, $R^3$, $R^4$ and $R^5$ are hydrogen.

36. The compound of claim 33 wherein $R^2$ and $R^4$ are hydrogen, $R^3$ is methoxy and $R^5$ is ethyl.

37. The compound of claim 33 wherein $R^2$, $R^4$ and $R^5$ are hydrogen and $R^3$ is methoxy.

38. The compound of claim 33 wherein $R^2$ and $R^3$ are hydrogen, $R^4$ is methoxy and $R^5$ is ethyl.

39. The compound of claim 33 wherein $R^2$, $R^3$ and $R^5$ are hydrogen and $R^4$ is methoxy.

40. The compound of claim 33 wherein $R^2$, $R^3$ and $R^5$ are hydrogen and $R^4$ is hydroxy.

41. The compound of claim 33 wherein $R^2$, $R^3$ and $R^5$ are hydrogen and $R^4$ is isobutyryloxy.

42. The compound of claim 33 wherein $R^2$ and $R^5$ are ethyl and $R^3$ and $R^4$ are hydrogen.

43. The (+) optical isomer of the compound of claim 42.

44. The (−) optical isomer of the compound of claim 42.

45. The compound of claim 33 wherein $R^2$ is ethyl and $R^3$, $R^4$ and $R^5$ are hydrogen.

46. The (+) optical isomer of the compound of claim 45.

47. The (−) optical isomer of the compound of claim 45.

48. The compound of claim 33 wherein $R^2$ is hydrogen, $R^3$ and $R^4$ are methoxy and $R^5$ is ethyl.

49. The compound of claim 33 wherein $R^2$ and $R^5$ are hydrogen and $R^3$ and $R^4$ are methoxy.

50. The compound of claim 33 wherein $R^2$ and $R^5$ are hydrogen and $R^3$ and $R^4$ are hydroxy.

51. The compound of claim 33 wherein $R^2$ is allyl, $R^3$ is hydrogen, $R^4$ is methoxy and $R^5$ is ethyl.

52. The (+) optical isomer of the compound of claim 51.

53. The (−) optical isomer of the compound of claim 51.

54. The compound of claim 33 wherein $R^2$ is allyl, $R^3$ and $R^5$ are hydrogen and $R^4$ is methoxy.

55. The (+) optical isomer of the compound of claim 54.

56. The (−) optical isomer of the compound of claim 54.

57. The compound of claim 33 wherein $R^2$ is formylmethyl, $R^3$ is hydrogen, $R^4$ is methoxy and $R^5$ is ethyl.

58. The (+) optical isomer of the compound of claim 57.

59. The (−) optical isomer of the compound of claim 57.

60. The compound of claim 33 wherein $R^2$ is dimethoxyethyl, $R^3$ is hydrogen, $R^4$ is methoxy and $R^5$ is ethyl.

61. The (+) optical isomer of the compound of claim 60.

62. The (−) optical isomer of the compound of claim 60.

63. A compound of the formula

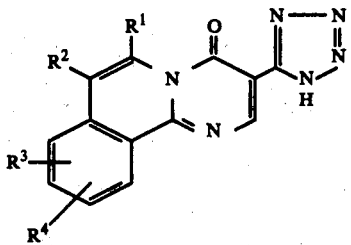

wherein $R^1$ is hydrogen, (lower)alkyl or phenyl, $R^2$ is hydrogen, (lower)alkyl, (lower)alkenyl, (lower)alkynyl, hydroxy, (lower)alkoxy, $R^6$—COO— in which $R^6$ is (lower)alkyl or phenyl, di(lower)alkoxyethyl, formylmethyl, —CH$_2$CH(OH)CH$_2$OH, hydroxyethyl, phenyl, benzyl, $C_3$-$C_6$ cycloalkyl-$C_1$-$C_2$ alkyl, $C_5$-$C_6$ cycloalkyl or halogen and $R^3$ and $R^4$ are each independently hydrogen, (lower)alkyl, hydroxy, (lower)alkoxy, $R^6$—COO— in which $R^6$ is (lower)alkyl or phenyl, halogen, (lower)alkenyl or trifluoromethyl, or $R^3$ and $R^4$ taken together are methylenedioxy, with the provisos that (1) $R^3$ and $R^4$ taken together may not be adjacent t-butyl and (2) when either of $R^3$ or $R^4$ is trifluoromethyl, the other must be hydrogen; or a pharmaceutically acceptable cationic salt thereof.

64. A compound of claim 63 wherein $R^1$ is hydrogen and $R^2$ is hydrogen, (lower)alkyl, (lower)alkenyl, hydroxy, (lower)alkoxy, $R^6$—COO— in which $R^6$ is (lower)alkyl or phenyl, di(lower)alkoxyethyl, formylmethyl, phenyl, benzyl, $C_5$-$C_6$ cycloalkyl or $C_3$-$C_6$ cycloalkyl-$C_1$-$C_2$ alkyl.

65. A compound of the formula

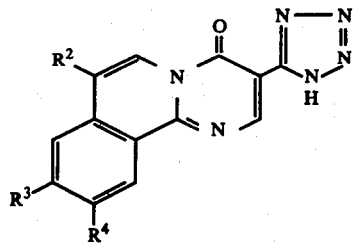

wherein $R^2$ is hydrogen, (lower)alkyl, (lower)alkenyl, hydroxy, (lower)alkoxy, $R^6$—COO— in which $R^6$ is (lower)alkyl, or phenyl, di(lower)alkoxyethyl, formylmethyl, phenyl, benzyl, $C_3$-$C_6$ cycloalkyl-$C_1$-$C_2$ alkyl or $C_5$-$C_6$ cycloalkyl and $R^3$ and $R^4$ are each independently hydrogen, (lower)alkyl, hydroxy, (lower)alkoxy, $R^6$—COO— in which $R^6$ is (lower)alkyl or phenyl, halogen, (lower)alkenyl or trifluoromethyl, or $R^3$ and $R^4$ taken together are methylenedioxy, with the provisos that (1) $R^3$ and $R^4$ taken together may not be adjacent t-butyl and (2) when either of $R^3$ and $R^4$ is trifluoromethyl, the other must be hydrogen; or a pharmaceutically acceptable cationic salt thereof.

66. A compound of the formula

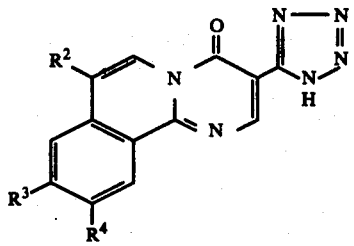

wherein $R^2$ is hydrogen, ethyl, hydroxy, allyl or n-propyl and $R^3$ and $R^4$ are each independently hydrogen or methoxy; or a pharmaceutically acceptable cationic salt thereof.

67. The compound of claim 66 wherein $R^2$, $R^3$ and $R^4$ are hydrogen.

68. The compound of claim 66 wherein $R^2$ is ethyl and $R^3$ and $R^4$ are hydrogen.

69. A compound of the formula

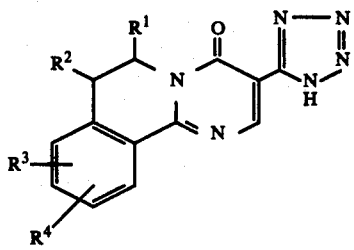

wherein $R^1$ is hydrogen, (lower)alkyl or phenyl, $R^2$ is hydrogen, (lower)alkyl, (lower)alkenyl, (lower)alkynyl, hydroxy, (lower)alkoxy, $R^6$—COO— in which $R^6$ is (lower)alkyl or phenyl, di(lower)alkoxyethyl, formylmethyl, —CH$_2$CH(OH)CH$_2$OH, hydroxyethyl, phenyl, benzyl, $C_3$-$C_6$ cycloalkyl-$C_1$-$C_2$ alkyl or $C_5$-$C_6$ cycloalkyl, $R^3$ and $R^4$ are each independently hydrogen, (lower)alkyl, hydroxy, (lower)alkoxy, $R^6$—COO— in which $R^6$ is (lower)alkyl or phenyl, halogen, (lower)alkenyl or trifluoromethyl, or $R^3$ and $R^4$ taken together are methylenedioxy, with the provisos that (1) $R^3$ and $R^4$ taken together may not be adjacent t-butyl and (2) when either of $R^3$ or $R^4$ is trifluoromethyl, the other must be hydrogen; or a pharmaceutically acceptable cationic salt thereof.

70. A compound of claim 69 wherein $R^1$ is hydrogen and $R^2$ is hydrogen, (lower)alkyl, (lower)alkenyl, hydroxy, (lower)alkoxy, $R^6$—COO— in which $R^6$ is (lower)alkyl or phenyl, di(lower)alkoxyethyl, formylmethyl, phenyl, benzyl, $C_3$-$C_6$ cycloalkyl-$C_1$-$C_2$ alkyl or $C_5$-$C_6$ cycloalkyl.

71. A compound of the formula

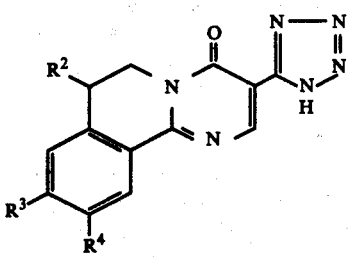

wherein $R^2$ is hydrogen, (lower)alkyl, (lower)alkenyl, hydroxy, (lower)alkoxy, $R^6$—COO— in which $R^6$ is (lower)alkyl or phenyl, di(lower)alkoxyethyl, formylmethyl, phenyl, benzyl, $C_3$-$C_6$ cycloalkyl-$C_1$-$C_2$ alkyl or $C_5$-$C_6$ cycloalkyl and $R^3$ and $R^4$ are each independently hydrogen, (lower)alkyl, hydroxy, (lower)alkoxy, $R^6$—COO— in which $R^6$ is (lower)alkyl or phenyl, halogen, (lower)alkenyl or trifluoromethyl, or $R^3$ and $R^4$ taken together are methylenedioxy, with the provisos that (1) $R^3$ and $R^4$ taken together may not be adjacent t-butyl and (2) when either of $R^3$ and $R^4$ is trifluoromethyl, the other must be hydrogen; or a pharmaceutically acceptable cationic salt thereof.

72. A compound of the formula

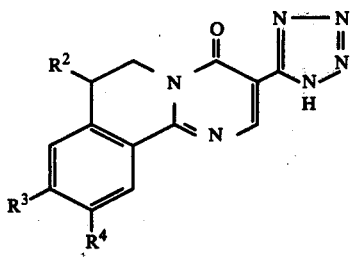

wherein $R^2$ is hydrogen, ethyl, allyl, formylmethyl or dimethoxyethyl and $R^3$ and $R^4$ are each independently hydrogen, methoxy, hydroxy or isobutyryloxy; or a pharmaceutically acceptable cationic salt thereof.

73. The compound of claim 72 wherein $R^2$ is ethyl and $R^3$ and $R^4$ are hydrogen.

74. The (+) optical isomer of the compound of claim 73.

75. The (−) optical isomer of the compound of claim 73.

76. The compound of claim 72 wherein $R^2$ is hydrogen and $R^3$ and $R^4$ are methoxy.

* * * * *

UNITED STATES PATENT AND TRADEMARK OFFICE
CERTIFICATE OF CORRECTION

PATENT NO. : 4,127,720
DATED : November 28, 1978
INVENTOR(S) : Peter Frederick Juby et al.

It is certified that error appears in the above-identified patent and that said Letters Patent are hereby corrected as shown below:

In Claim 27, lines 30-38, change the double bond between substituents $R^1$ and $R^2$ to a single bond.

Signed and Sealed this

*Twenty-sixth* Day of *February 1980*

[SEAL]

*Attest:*

SIDNEY A. DIAMOND

*Attesting Officer*  *Commissioner of Patents and Trademarks*